United States Patent
Kato et al.

(10) Patent No.: US 12,338,407 B2
(45) Date of Patent: Jun. 24, 2025

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Tsuyoshi Kato, Ichihara (JP); Ayano Asano, Ichihara (JP); Natsumi Shibata, Ichihara (JP); Daisuke Yagyu, Ichihara (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 17/772,043

(22) PCT Filed: Nov. 6, 2020

(86) PCT No.: PCT/JP2020/041613
§ 371 (c)(1),
(2) Date: Apr. 26, 2022

(87) PCT Pub. No.: WO2021/090940
PCT Pub. Date: May 14, 2021

(65) Prior Publication Data
US 2023/0002696 A1 Jan. 5, 2023

(30) Foreign Application Priority Data
Nov. 7, 2019 (JP) .................... 2019-202285

(51) Int. Cl.
*C10M 105/54* (2006.01)
*C07C 43/13* (2006.01)
(Continued)

(52) U.S. Cl.
CPC ......... *C10M 105/54* (2013.01); *C07C 43/137* (2013.01); *C07D 309/12* (2013.01);
(Continued)

(58) Field of Classification Search
CPC ............... G11B 5/7257; C10M 105/54; C10M 2211/0425; C07C 43/137; C07D 309/12; C10N 2040/18
See application file for complete search history.

(56) References Cited

U.S. PATENT DOCUMENTS 4,526,833 A 7/1985 Burguette et al.
6,323,163 B1 11/2001 Sasaki et al.
(Continued)

FOREIGN PATENT DOCUMENTS

CN 101121908 A 2/2008
CN 114599631 A 6/2022
(Continued)

OTHER PUBLICATIONS

International Search Report for PCT/JP2020/041613, dated Dec. 28, 2020.
(Continued)

*Primary Examiner* — Holly Rickman
(74) *Attorney, Agent, or Firm* — Sughrue Mion, PLLC

(57) ABSTRACT

This fluorine-containing ether compound is represented by formula (1) shown below.

$$R^1-CH_2-R^2-CH_2-R^3 \tag{1}$$

In formula (1), $R^2$ is a perfluoropolyether chain represented by a formula (2) shown below. $R^1$ is a terminal group that is bonded to $R^2$ via a $CH_2$ group, and is represented by a formula (3) shown below. $R^3$ is bonded to $R^2$ via a $CH_2$ group, is a terminal group having at least one hydroxyl group, and may be the same as, or different from, $R^1$.

$$-(CF_2)_{p-1}-O-((CF_2)_pO)_q-(CF_2)_{p-1}- \tag{2}$$

In formula (2), p represents an integer of 2 to 3, and q indicates the average polymerization degree and is a number within a range from 1 to 20.

$$-O(CH_2-CH(OH)-CH_2-O)_2-CH_2-(CH_2)_n-OH \tag{3}$$

In formula (3), n represents an integer of 1 to 8.

10 Claims, 1 Drawing Sheet

(51) Int. Cl.
*C07D 309/12* (2006.01)
*G11B 5/725* (2006.01)
*C10N 40/18* (2006.01)

(52) U.S. Cl.
CPC ... *G11B 5/7257* (2020.08); *C10M 2211/0425* (2013.01); *C10N 2040/18* (2013.01)

(56) References Cited

U.S. PATENT DOCUMENTS

| | | | |
|---|---|---|---|
| 10,803,898 B2 | 10/2020 | Fukumoto et al. | |
| 11,011,200 B2 | 5/2021 | Uetake et al. | |
| 11,220,649 B2 | 1/2022 | Fukumoto et al. | |
| 11,225,624 B2* | 1/2022 | Kato | C10M 107/38 |
| 11,261,394 B2* | 3/2022 | Kato | C10M 107/38 |
| 11,279,664 B2 | 3/2022 | Yagyu et al. | |
| 11,427,779 B2 | 8/2022 | Yamaguchi et al. | |
| 11,639,330 B2* | 5/2023 | Nanko | C07C 255/19 |
| | | | 428/848 |
| 2004/0235685 A1 | 11/2004 | Russo et al. | |
| 2005/0123855 A1 | 6/2005 | Hegel | |
| 2005/0197408 A1* | 9/2005 | Shirakawa | C10M 107/38 |
| | | | 514/723 |
| 2006/0111251 A1 | 5/2006 | Tonelli et al. | |
| 2009/0281250 A1 | 11/2009 | Desimone et al. | |
| 2010/0233513 A1 | 9/2010 | Imai et al. | |
| 2010/0261039 A1 | 10/2010 | Itoh et al. | |
| 2012/0008228 A1 | 1/2012 | Mabuchi et al. | |
| 2012/0225217 A1 | 9/2012 | Itoh et al. | |
| 2013/0209837 A1 | 8/2013 | Sagata et al. | |
| 2015/0274960 A1 | 10/2015 | Fukuda et al. | |
| 2015/0371672 A1 | 12/2015 | Sagata | |
| 2016/0068778 A1 | 3/2016 | Conley et al. | |
| 2017/0152456 A1 | 6/2017 | Sagata et al. | |
| 2017/0260472 A1* | 9/2017 | Sagata | C10M 107/38 |
| 2018/0009773 A1 | 1/2018 | Uetake et al. | |
| 2018/0022851 A1 | 1/2018 | Takao et al. | |
| 2018/0047419 A1* | 2/2018 | Fukumoto | C08G 65/2639 |
| 2018/0127543 A1 | 5/2018 | Watanabe et al. | |
| 2019/0084911 A1 | 3/2019 | Yagyu et al. | |
| 2019/0185621 A1 | 6/2019 | Naitou et al. | |
| 2019/0352573 A1 | 11/2019 | Hatta et al. | |
| 2019/0382675 A1 | 12/2019 | Fukumoto et al. | |
| 2019/0382676 A1 | 12/2019 | Yamaguchi et al. | |
| 2020/0010619 A1 | 1/2020 | Minami et al. | |
| 2021/0062101 A1 | 3/2021 | Kato et al. | |
| 2021/0062102 A1 | 3/2021 | Kato et al. | |
| 2021/0188766 A1 | 6/2021 | Nanko et al. | |
| 2022/0169941 A1 | 6/2022 | Shibata | |
| 2022/0372390 A1 | 11/2022 | Ayano | |
| 2023/0090239 A1 | 3/2023 | Nanko | |

FOREIGN PATENT DOCUMENTS

| | | |
|---|---|---|
| EP | 1 479 753 A2 | 11/2004 |
| EP | 3 081 549 A1 | 10/2016 |
| JP | 61-126052 A | 6/1986 |
| JP | 11-60720 A | 3/1999 |
| JP | 11-71440 A | 3/1999 |
| JP | 2866622 B2 | 3/1999 |
| JP | 2000-264883 A | 9/2000 |
| JP | 2001-134924 A | 5/2001 |
| JP | 2001-209924 A | 8/2001 |
| JP | 2002-69037 A | 3/2002 |
| JP | 2004-115640 A | 4/2004 |
| JP | 2004-346318 A | 12/2004 |
| JP | 2006-131874 A | 5/2006 |
| JP | 2009-266360 A | 11/2009 |
| JP | 2010-143855 A | 7/2010 |
| JP | 2010-241831 A | 10/2010 |
| JP | 4632144 B2 | 2/2011 |
| JP | 2012-009090 A | 1/2012 |
| JP | 2012-33253 A | 2/2012 |
| JP | 2013-163667 A | 8/2013 |
| JP | 2013-181014 A | 9/2013 |
| JP | 2013-181140 A | 9/2013 |
| JP | 2014-509677 A | 4/2014 |
| JP | 5465454 B2 | 4/2014 |
| JP | 5613916 B2 | 10/2014 |
| JP | 5909837 B2 | 4/2016 |
| JP | 6122191 B1 | 4/2017 |
| JP | 2018-002673 A | 1/2018 |
| JP | 2018-024614 A | 2/2018 |
| JP | 2018-035348 A | 3/2018 |
| WO | 98/17617 A1 | 4/1998 |
| WO | 2006/011387 A1 | 2/2006 |
| WO | 2009/035075 A1 | 3/2009 |
| WO | 2009/123043 A1 | 10/2009 |
| WO | 2011/099131 A1 | 8/2011 |
| WO | 2012/170009 A2 | 12/2012 |
| WO | 2015/087615 A1 | 6/2015 |
| WO | 2015/199037 A1 | 12/2015 |
| WO | 2016/084781 A1 | 6/2016 |
| WO | 2017/145995 A1 | 8/2017 |
| WO | 2017/154403 A1 | 9/2017 |
| WO | 2018/116742 A1 | 6/2018 |
| WO | 2018/139058 A1 | 8/2018 |
| WO | 2018/139174 A1 | 8/2018 |
| WO | 2018/147017 A1 | 8/2018 |
| WO | 2018/159232 A1 | 9/2018 |
| WO | 2019/039200 A1 | 2/2019 |
| WO | 2019/049585 A1 | 3/2019 |
| WO | 2019/054148 A1 | 3/2019 |
| WO | 2019/087548 A1 | 5/2019 |

OTHER PUBLICATIONS

International Search Report for PCT/JP2020/033971 dated Nov. 24, 2020 [PCT/ISA/210].
International Search Report for PCT/JP2021/003708 dated Mar. 23, 2021.
Office Action issued Dec. 21, 2022 in U.S. Appl. No. 17/274,466.
Office Action Non-Final dated Jan. 28, 2021, issued in U.S. Appl. U.S. Appl. No. 16/480,464.
"Cihai Sciences vol. 1" Edited by Cihai Editorial Committee, Shanghai Lexicographical Publishing House, Aug. 30, 1980, p. 329 (3 pages total).
Notice of Reasons for Rejection dated Dec. 24, 2019 from the Japanese Patent Office in Application No. 2016-133653.
International Search Report for PCT/JP2017/003165 dated May 9, 2017.
International Search Report for PCT/JP2019/033697 dated Nov. 5, 2019.
Notice of Allowance dated Feb. 8, 2021 from the US Patent & Trademark Office in U.S. Appl. No. 15/640,729.
Notice of Allowance dated Nov. 16, 2021 from the US & Patent & Trademark Office in U.S. Appl. No. 16/082,349.
Office Action dated Dec. 2, 2020 from the China National Intellectual Property Administration in CN Application No. 201780012469.9.
Office Action dated Jun. 10, 2019 from the US & Patent & Trademark Office in U.S. Appl. No. 15/640,729.
Office Action dated Jun. 8, 2021 from the US & Patent & Trademark Office in U.S. Appl. No. 16/082,349.
Office Action dated Mar. 4, 2021 from the US & Patent & Trademark Office in U.S. Appl. No. 15/640,729.
Office Action dated May 13, 2020 from the US & Patent & Trademark Office in U.S. Appl. No. 15/640,729.
Office Action dated May 25, 2021 from the China National Intellectual Property Administration in CN Application No. 201780012469.9.
Office Action dated Nov. 12, 2020 from the US & Patent & Trademark Office in U.S. Appl. No. 15/640,729.
Office Action dated Oct. 29, 2019 from the US & Patent & Trademark Office in U.S. Appl. No. 15/640,729.
Advisory Action Dated Aug. 11, 2021 Issued in U.S. Appl. No. 16/480,464.
International Search Report for PCT/JP2017/043451 dated Feb. 27, 2018 [PCT/ISA/210].

(56) References Cited

OTHER PUBLICATIONS

International Search Report of PCT/JP2020/010759 dated May 26, 2020 [PCT/ISA/210].
Notice of Allowance Dated Sep. 10, 2021 issued in U.S. Appl. No. 16/480,464.
Office Action dated Mar. 11, 2021 from the China National Intellectual Property Administration in CN Application No. 201780070908.1.
Office Action Final Dated Apr. 16, 2021 Issued in U.S. Appl. No. 16/480,464.
Restriction Election Requirement Dated Nov. 23, 2020 Issued in U.S. Appl. No. 16/480,464.
Office Action issued Jan. 19, 2023 in U.S. Appl. No. 17/437,251.
International Search Report for PCT/JP2018/000071 dated Mar. 6, 2018 [PCT/ISA/210].
Notice of Allowance issued May 5, 2022 in U.S. Appl. No. 16/480,483.
Office Action issued Jan. 19, 2022 in U.S. Appl. No. 16/480,483.
Office Action issued Jun. 21, 2021 in U.S. Appl. No. 16/480,483.
Office Action issued Oct. 25, 2022 in U.S. Appl. No. 17/274,702.
International Search Report for PCT/JP2019/033700 dated Nov. 12, 2019 [PCT/ISA/210].
Office Action issued Jul. 23, 2021 in U.S. Appl. No. 16/644,586.
International Search Report for PCT/JP2018/031161, dated Nov. 27, 2018 (PCT/ISA/210).
Notice of Allowance issued Feb. 9, 2023 in U.S. Appl. No. 17/274,702.
Notice of Allowance issued Nov. 9, 2021 in U.S. Appl. No. 16/644,586.
Office Action issued Jun. 7, 2023 in U.S. Appl. No. 17/797,177.
Supplemental Notice of Allowance issued Dec. 2, 2021 in U.S. Appl. No. 16/644,586.

* cited by examiner

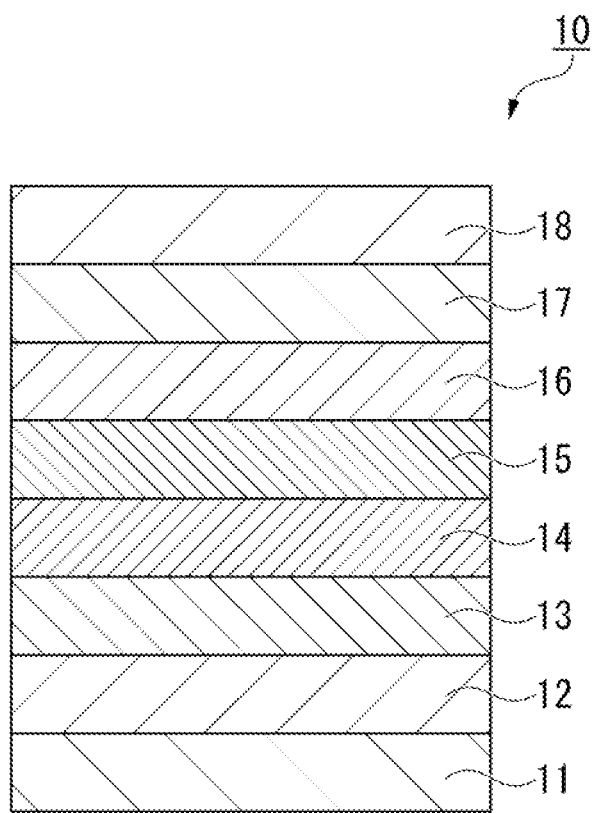

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2020/041613 filed Nov. 6, 2020, claiming priority based on Japanese Patent Application No. 2019-202285 filed Nov. 7, 2019, the content of which is incorporated herein by reference.

The present invention relates to a fluorine-containing ether compound that is suitable for lubricant applications in magnetic recording media, and a magnetic recording medium lubricant and a magnetic recording medium that include the fluorine-containing ether compound.

BACKGROUND ART

In order to improve the recording density of magnetic recording and playback devices, the development of magnetic recording media that are suited to high recording densities continues to progress.

Conventional magnetic recording media include media obtained by forming a recording layer on a substrate, and then forming a protective layer of carbon or the like on the recording layer. The protective layer protects the information recorded on the recording layer, and also enhances the slidability of the magnetic head. However, satisfactory durability for the magnetic recording medium cannot be achieved simply by providing a protective layer on the recording layer. Therefore, a lubricant layer is generally formed by applying a lubricant to the surface of the protective layer.

Examples of lubricants that have been proposed for the lubricant that is used when forming the lubricant layer of a magnetic recording medium include lubricants containing a fluorine-based polymer having a repeating structure containing $CF_2$ and having polar groups such as hydroxyl groups at the polymer terminals (for example, see Patent Documents 1 and 2).

Specifically, Patent Document 1 discloses a compound having a plurality of hydroxyl groups at both of the terminal portions.

Further, Patent Document 2 discloses a compound having a perfluoropolyether main chain, wherein a terminal group of the molecule contains at least two polar groups, each of those polar groups is bonded to a different carbon atom, and the carbon atoms to which the polar groups are bonded are linked via a linking group containing a carbon atom to which no polar groups are bonded.

PRIOR ART LITERATURE

Patent Documents

Patent Document 1: Japanese Patent (Granted) Publication No. 4632144
Patent Document 2: Japanese Unexamined Patent Application, First Publication No. 2018-24614

DISCLOSURE OF INVENTION

Problems to be Solved by the Invention

In magnetic recording and playback devices, in addition to improved recording density, higher reliability would also be desirable, such as an improvement in chemical substance resistance and pickup suppression. Chemical substance resistance refers to resistance to contamination of the magnetic recording medium by environmental substances, whereas pickup suppression refers to the ability to inhibit adhesion of the fluorine-containing ether compound in the lubricant layer to the magnetic head as foreign matter (smear).

The present invention has been developed in light of the above circumstances, and has an object of providing a fluorine-containing ether compound that can be used favorably as a material for a magnetic recording medium lubricant that is capable of forming a lubricant layer which has good adhesion to the protective layer, can suppress pickup, and exhibits excellent chemical substance resistance.

Further, the present invention also has an object of providing a magnetic recording medium lubricant containing the fluorine-containing ether compound of the present invention.

Furthermore, the present invention also has an object of providing a magnetic recording medium of superior reliability and durability having a lubricant layer containing the fluorine-containing ether compound of the present invention.

Means for Solving the Problems

The inventors of the present invention conducted intensive research aimed at achieving the above objects.

As a result, they discovered that the above objects could be achieved by using a fluorine-containing ether compound in which a plurality of hydroxyl groups are disposed in a specific structure on at least one of the terminals of a perfluoropolyether (hereafter sometimes abbreviated as "PFPE") chain having rigidity, and were thus able to complete the present invention.

In other words, the present invention relates to the following items.

A fluorine-containing ether compound represented by a formula (1) shown below.

$$R^1\text{—}CH_2\text{—}R^2\text{—}CH_2\text{—}R^3 \quad (1)$$

(In formula (1), $R^2$ is a perfluoropolyether chain represented by a formula (2) shown below. $R^1$ is a terminal group that is bonded to $R^2$ via a $CH_2$ group, and is represented by a formula (3) shown below. $R^3$ is bonded to $R^2$ via a $CH_2$ group, is a terminal group having at least one hydroxyl group, and may be the same as, or different from, $R^1$.

$$\text{—}(CF_2)_{p-1}\text{—}O\text{—}((CF_2)_pO)_q\text{—}(CF_2)_{p-1}\text{—} \quad (2)$$

(In formula (2), p represents an integer of 2 to 3, and q indicates the average polymerization degree and is a number within a range from 1 to 20.)

[Chemical formula 1]

$$\cdots O\left(\begin{array}{c}\\ \\ OH\end{array}\right)O\left.\begin{array}{c}\\ \\ \end{array}\right)_2 \!\!\!\!\! \diagdown_n\!\!\!\!\text{OH} \quad (3)$$

(In formula (3), n represents an integer of 1 to 8.)

The fluorine-containing ether compound according to [1], wherein $R^3$ in the formula (1) is a terminal group represented by the above formula (3).

The fluorine-containing ether compound according to [2], wherein the compound represented by the formula (1) is a compound represented by one of formulas (D) to (G) shown below.

[Chemical formula 2]

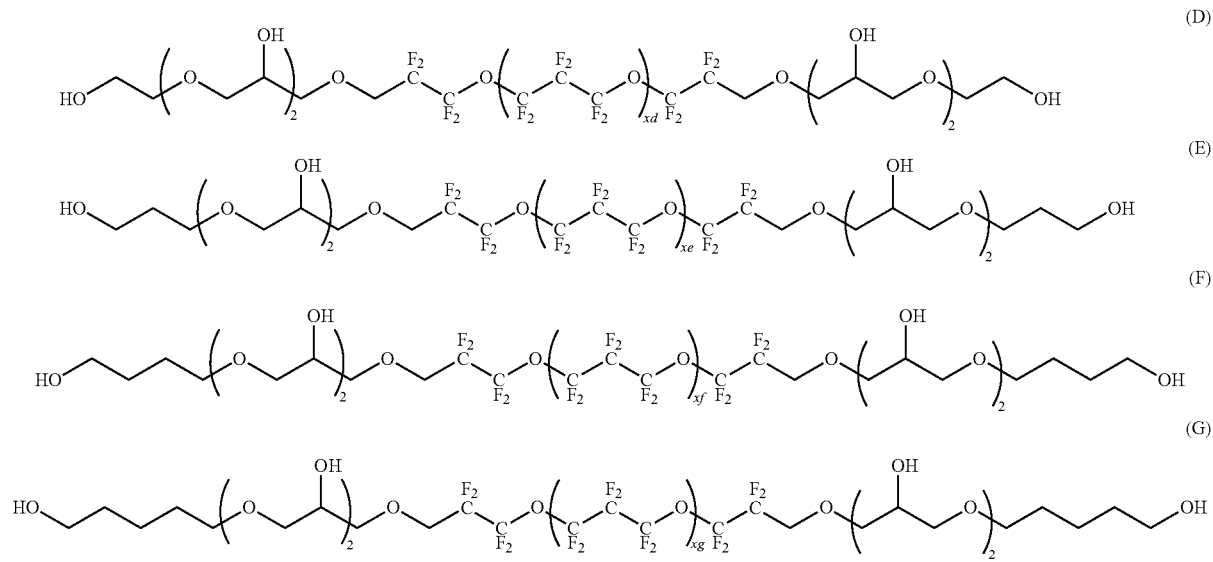

(In formula (D), xd indicates the average polymerization degree, and represents a number from 1 to 14.)
(In formula (E), xe indicates the average polymerization degree, and represents a number from 1 to 14.)
(In formula (F), xf indicates the average polymerization degree, and represents a number from 1 to 14.)
(In formula (G), xg indicates the average polymerization degree, and represents a number from 1 to 14.)

The fluorine-containing ether compound according to [2], wherein the ether compound represented by the formula (1) is a compound represented by one of formulas (N) to (Q) shown below.

[Chemical formula 3]

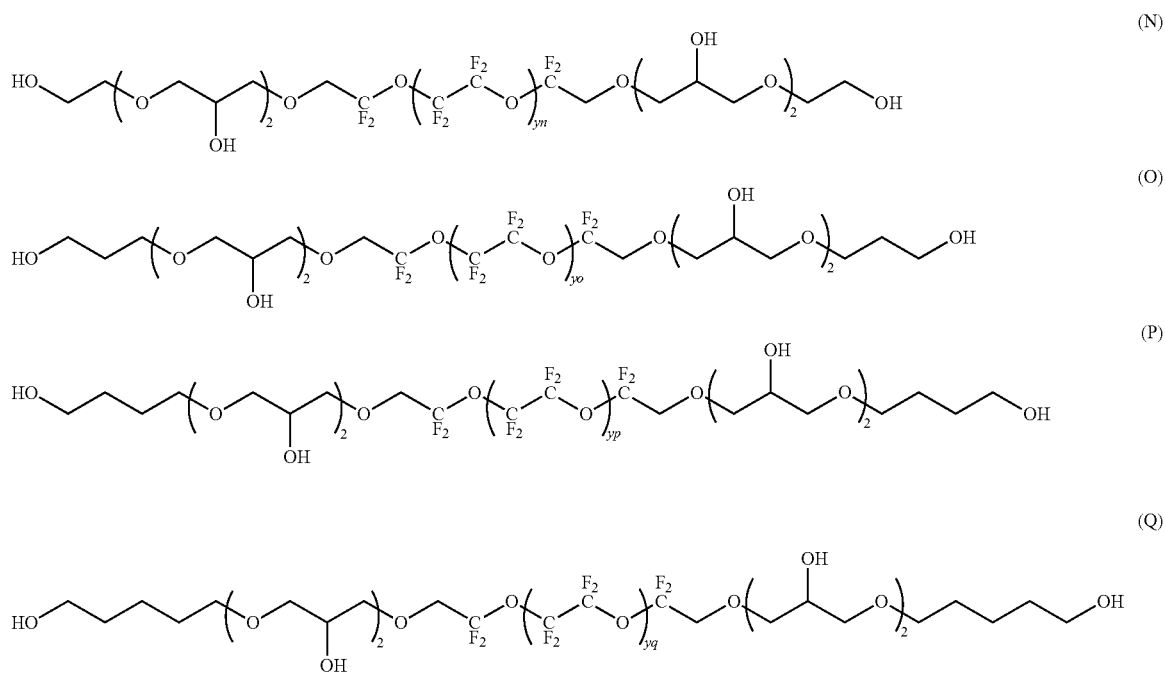

(In formula (N), yn indicates the average polymerization degree, and represents a number from 1 to 20.)
(In formula (O), yo indicates the average polymerization degree, and represents a number from 1 to 20.)
(In formula (P), yp indicates the average polymerization degree, and represents a number from 1 to 20.)
(In formula (Q), yq indicates the average polymerization degree, and represents a number from 1 to 20.)

The fluorine-containing ether compound according to [1], wherein $R^3$ in the formula (1) is a hydroxyl group, or a terminal group represented by formula (4-1) or formula (4-2) shown below.

$$—O—CH_2—CH(OH)—CH_2—OH \quad (4\text{-}1)$$

$$—O—CH_2—CH(OH)—CH_2—O—(CH_2)_k—OH \quad (4\text{-}2)$$

(In formula (4-2), k represents an integer of 1 to 5.)

The fluorine-containing ether compound according to [5], wherein $R^3$ in the formula (1) is a terminal group represented by the formula (4-2).

The fluorine-containing ether compound according to [5], wherein the ether compound represented by the formula (1) is a compound represented by one of formulas (C) and (H) shown below.

[Chemical formula 4]

$$HO\text{-}CH_2CH_2\text{-}O\text{-}CH_2\text{-}CH(OH)\text{-}CH_2\text{-}O\text{-}CH_2\text{-}CF_2\text{-}O\text{-}(CF_2CF_2\text{-}O)_{xc}\text{-}CF_2\text{-}CH_2\text{-}O\text{-}(CH_2\text{-}CH(OH)\text{-}O)_2\text{-}OH \quad (C)$$

$$HO\text{-}(CH_2)_3\text{-}O\text{-}CH_2\text{-}CH(OH)\text{-}CH_2\text{-}O\text{-}CH_2\text{-}CF_2\text{-}O\text{-}(CF_2CF_2\text{-}O)_{xh}\text{-}CF_2\text{-}CH_2\text{-}O\text{-}(CH_2\text{-}CH(OH)\text{-}O)_2\text{-}OH \quad (H)$$

(In formula (C), xc indicates the average polymerization degree, and represents a number from 1 to 14.)
(In formula (H), xh indicates the average polymerization degree, and represents a number from 1 to 14.)

The fluorine-containing ether compound according to [5], wherein the ether compound represented by the formula (1) is a compound represented by one of formulas (M) and (R) shown below.

[Chemical formula 5]

$$HO\text{-}CH_2CH_2\text{-}O\text{-}CH_2\text{-}CH(OH)\text{-}CH_2\text{-}O\text{-}CH_2\text{-}CF_2\text{-}O\text{-}(CF_2CF_2\text{-}O)_{ym}\text{-}CF_2\text{-}CH_2\text{-}O\text{-}(CH_2\text{-}CH(OH)\text{-}O)_2\text{-}OH \quad (M)$$

$$HO\text{-}(CH_2)_3\text{-}O\text{-}CH_2\text{-}CH(OH)\text{-}CH_2\text{-}O\text{-}CH_2\text{-}CF_2\text{-}O\text{-}(CF_2CF_2\text{-}O)_{yr}\text{-}CF_2\text{-}CH_2\text{-}O\text{-}(CH_2\text{-}CH(OH)\text{-}O)_2\text{-}OH \quad (R)$$

(In formula (M), ym indicates the average polymerization degree, and represents a number from 1 to 20.)

(In formula (R), yr indicates the average polymerization degree, and represents a number from 1 to 20.)

The fluorine-containing ether compound according to any one of [1] to [8], having a number average molecular weight within a range from 400 to 3,000.

A lubricant for a magnetic recording medium, the lubricant containing the fluorine-containing ether compound according to any one of [1] to [8].

A magnetic recording medium containing at least a magnetic layer, a protective layer and a lubricant layer provided sequentially on a substrate, wherein the lubricant layer contains the fluorine-containing ether compound according to any one of [1] to [8].

The magnetic recording medium according to [11], wherein the average thickness of the lubricant layer is within a range from 0.5 nm to 1.5 nm.

Effects of the Invention

The fluorine-containing ether compound of the present invention is ideal as a material for a lubricant for a magnetic recording medium.

Since the lubricant for a magnetic recording medium according to the present invention contains the fluorine-containing ether compound of the present invention, a lubricant layer can be formed that has good adhesion to the protective layer, can suppress pickup, and exhibits excellent chemical substance resistance.

The magnetic recording medium of the present invention is provided with a lubricant layer that has good adhesion to the protective layer, can suppress pickup and exhibits excellent chemical substance resistance, and therefore exhibits excellent reliability and durability.

BRIEF DESCRIPTION OF THE DRAWINGS

The FIGURE is a schematic cross-sectional view illustrating one embodiment of a magnetic recording medium of the present invention.

EMBODIMENTS FOR CARRYING OUT THE INVENTION

The fluorine-containing ether compound, the lubricant for a magnetic recording medium (hereafter sometimes abbreviated as simply "the lubricant"), and the magnetic recording medium according to the present invention are described below in detail. However, the present invention is not limited solely to the embodiments described below.

[Fluorine-Containing Ether Compound]

The fluorine-containing ether compound of an embodiment of the present invention is represented by formula (1) shown below.

$$R^1-CH_2-R^2-CH_2-R^3 \quad (1)$$

(In formula (1), $R^2$ is a perfluoropolyether chain represented by a formula (2) shown below. $R^1$ is a terminal group that is bonded to $R^2$ via a $CH_2$ group, and is represented by a formula (3) shown below. $R^3$ is bonded to $R^2$ via a $CH_2$ group, is a terminal group having at least one hydroxyl group, and may be the same as, or different from, $R^1$.

$$-(CF_2)_{p-1}-O-((CF_2)_pO)_q-(CF_2)_{p-1}- \quad (2)$$

(In formula (2), p represents an integer of 2 to 3, and q indicates the average polymerization degree and is a number within a range from 1 to 20.)

[Chemical formula 6]

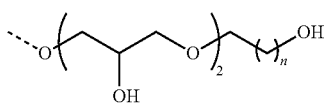

(3)

(In formula (3), n represents an integer of 1 to 8.)

In formula (2), p represents an integer of 2 to 3, and q indicates the average polymerization degree and is a number within a range from 1 to 20.

A value of p that falls within this range is ideal for forming a thin film with a thickness of 10 Å or less. If p is less than 2, then the rigidity of the perfluoropolyether chain tends to be insufficient, and the fluorine-containing ether compound is more likely to aggregate on top of the protective layer. Further, if p exceeds 3, then the perfluoropolyether chain becomes overly rigid, and achieving suitable adhesion to the protective layer becomes difficult.

In this embodiment, because the value of p in formula (2) is an integer of 2 to 3, and q which indicates the average polymerization degree is a number within a range from 1 to 20, the number average molecular weight of the fluorine-containing ether compound falls within a preferred range. Further, because p in formula (2) is an integer of 2 to 3, and q which indicates the average polymerization degree is a number from 1 to 20, the ratio between the number of oxygen atoms (the number of ether bonds (—O—)) relative to the number of carbon atoms in the PFPE chain is appropriate, yielding a fluorine-containing ether compound having suitable rigidity.

Furthermore, because p in formula (2) is an integer of 2 to 3, and q which indicates the average polymerization degree is a number from 1 to 20, the orientation of the polar groups in the fluorine-containing ether compound applied to the protective layer is more easily maintained by the rigidity of the PFPE chain, meaning the fluorine-containing ether compound is unlikely to aggregate on top of the protective layer. As a result, by using the fluorine-containing ether compound of this embodiment, a lubricant layer having the thin thickness can be formed on the protective layer with a favorable coverage rate, and the PFPE chain can form a loop structure on top of the protective layer. When p in formula (2) is 3, the average degree of polymerization q is preferably within a range from 1 to 14, and more preferably from 4 to 10. When p in formula (2) is 2, the average degree of polymerization q is preferably within a range from 5 to 16, and more preferably from 6 to 12.

The terminal group $R^1$ represented by formula (3) in formula (1) is an organic terminal group of 8 to 15 carbon atoms containing three hydroxyl groups, wherein each hydroxyl group is bonded to a different carbon atom, and the carbon atoms to which the hydroxyl groups are bonded are linked via linking groups containing a carbon atom to which a hydroxyl group is not bonded.

The value of n in formula (3) is an integer of 1 to 8. The value of n is preferably from 1 to 4, more preferably from 2 to 4, and even more preferably 2 or 3. When the value of n falls within this range, the adhesion with the protective layer is favorable, and adhesion of the fluorine-containing ether compound to the magnetic head as foreign matter (smear) can be prevented.

In those cases where $R^3$ in formula (1) is a terminal group represented by the above formula (3), the values of n in $R^1$ and $R^3$ may be the same or different. When $R^3$ is a terminal group represented by the formula (3), it is preferable that the values of n in $R^1$ and $R^3$ are the same, as this yields a fluorine-containing ether compound represented by formula (1) in which the PFPE chain readily forms a loop structure on top of the protective layer, and also enables the compound to be produced in a small number of production steps.

In those cases where $R^3$ in formula (1) is a terminal group that is different from $R^1$, the number of hydroxyl groups included in the terminal group represented by $R^3$ is preferably 1 or 2, and more preferably 2.

The number of carbon atoms contained in the terminal group represented by $R^3$ is preferably not more than 10, and more preferably 8 or fewer. The terminal group represented by $R^3$ may be a group that contains no fluorine atoms.

Those cases where the terminal group represented by $R^3$ contains no more than 10 carbon atoms and includes 1 or 2 hydroxyl groups yield a particularly good balance with a terminal group represented by $R^1$ containing 8 to 15 carbon atoms and including 3 hydroxyl groups, meaning the PFPE chain can easily form a loop structure on top of the protective layer, and superior adhesion with the protective layer can be achieved.

The terminal group represented by $R^3$ preferably does not have a double bond or triple bond. Further, in the chain-like structure of the terminal group represented by $R^3$, a hydroxyl group is preferably located at the terminal portion on the opposite side from $R^2$. In such cases, a hydroxyl group is positioned at each of the absolute terminals of the fluorine-containing ether compound represented by formula (1), and a stronger adhesion to the protective layer can be achieved.

The polar group(s) contained in the terminal group represented by $R^3$ are preferably only hydroxyl group(s). When the polar group(s) contained in the terminal group represented by $R^3$ are only hydroxyl group(s), the balance with the terminal group represented by $R^1$ becomes favorable.

$R^3$ is preferably a hydroxyl group, or a terminal group represented by either of formula (4-1) and formula (4-2) shown below.

—O—CH$_2$—CH(OH)—CH$_2$— OH (4-1)

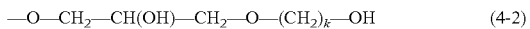
—O—CH$_2$—CH(OH)—CH$_2$—O—(CH$_2$)$_k$—OH (4-2)

(In formula (4-2), k represents an integer of 1 to 5.)

Among these, $R^3$ is more preferably represented by formula (4-1) or formula (4-2), and is most preferably represented by formula (4-2).

The terminal groups represented by formula (4-1) and formula (4-2) each contain two hydroxyl groups. When $R^3$ is a terminal group represented by formula (4-1) or formula (4-2), the two hydroxyl groups contained in $R^3$ and the hydroxyl groups contained in $R^1$ enable the compound to adhere to the protective layer at both terminals of the PFPE chain. Moreover, when $R^3$ is represented by formula (4-2), the two hydroxyl groups are bonded to different carbon atoms, and the carbon atoms to which the hydroxyl groups are bonded are linked via a linking group containing a carbon atom to which a hydroxyl group is not bonded. Moreover, an ether bond is also included between the carbon atoms to which the hydroxyl groups are bonded. As a result, when $R^3$ is represented by formula (4-2), the adhesion to the protective layer and the coating properties improve even further.

The value of k in formula (4-2) is an integer of 1 to 5. Provided the value of k falls within this range, the adhesion with the protective layer is favorable. The value of k is preferably an integer of 2 to 4, and more preferably either 2 or 3. When the value of k is either 2 or 3, the distance between the carbon atoms to which the hydroxyl groups are bonded is ideal, and the adhesion to the protective layer and the coating properties improve even further.

$R^1$ in the fluorine-containing ether compound represented by formula (1) has three hydroxyl groups. $R^3$ in the fluorine-containing ether compound represented by formula (1) has at least one hydroxyl group, and preferably has 1 or 2 hydroxyl groups.

In the fluorine-containing ether compound represented by formula (1), in those cases where $R^3$ is a terminal group represented by the same formula (3) as $R^1$, the total number of hydroxyl groups in formula (1) is 6. Further, in the fluorine-containing ether compound represented by formula (1), in those cases where $R^3$ is a terminal group that is different from $R^1$, the total number of hydroxyl groups in formula (1) is at least 4, is preferably 4 or 5, and is more preferably 5.

In the fluorine-containing ether compound represented by formula (1), when the total number of hydroxyl groups falls within the above range, the adhesion is favorable, and adhesion to the magnetic head as foreign matter (smear) can be prevented. Particularly in those cases where the total number of hydroxyl groups is 5 or 6, favorable adhesion can be achieved, and the pickup suppression effect is enhanced.

$R^1$ and $R^3$ in formula (1) may be selected appropriately in accordance with the performance and the like required of the lubricant containing the fluorine-containing ether compound.

When a lubricant containing the fluorine-containing ether compound of an embodiment of the present invention is used to form a lubricant layer on the protective layer of a magnetic recording medium, the reasons that including the PFPE chain represented by $R^2$ and the terminal group $R^1$ linked to $R^2$ in the fluorine-containing ether compound yields a lubricant layer which has good adhesion to the protective layer, can suppress pickup, and exhibits excellent chemical substance resistance are described below.

As shown in formula (1), the fluorine-containing ether compound of an embodiment of the present invention has a PFPE chain represented by $R^2$. In a lubricant layer containing the fluorine-containing ether compound of this embodiment, the PFPE chain represented by $R^2$ coats the surface of the protective layer, and also imparts lubricity to the lubricant layer, thereby reducing the frictional force between the magnetic head and the protective layer. Moreover, in a lubricant layer containing the fluorine-containing ether compound of this embodiment, the PFPE chain represented by formula (2), which has a repeating unit of good rigidity formed from a linear fluorinated alkyl ether chain, adheres (adsorbs) to the protective layer via the hydroxyl groups of the terminal groups positioned at both ends of the PFPE chain. Accordingly, the PFPE chain can form a loop structure on top of the protective layer. As a result, a lubricant layer that exhibits favorable adhesion to the protective layer is obtained.

Further, $R^1$ in formula (1) is a terminal group that is bonded to $R^2$ via a CH$_2$ group, and is represented by formula (3). In $R^1$ represented by formula (3), the carbon atoms to which the hydroxyl groups are bonded are linked together by linking groups containing a carbon atom to which a hydroxyl group is not bonded. As a result, in those cases where the protective layer to which the lubricant is applied is formed from carbon or a nitrogen-containing carbon, the following two effects are achieved. Firstly, the lubricant spreads readily across the protective layer without any aggregation of the hydroxyl groups of $R^1$, meaning the coating properties can be more easily improved. Secondly, the three hydroxyl groups of $R^1$ orient more readily in the same direction relative to the surface of the protective layer, producing a three-dimensional arrangement that enables the hydroxyl groups to adhere more readily to the protective layer surface.

Accordingly, it is thought that a lubricant layer containing the fluorine-containing ether compound of an embodiment of the present invention is able to exhibit more favorable adhesion to the protective layer, better suppress pickup, and also exhibit excellent chemical substance resistance, particularly in those cases where the protective layer is formed from carbon or a nitrogen-containing carbon.

Specifically, the fluorine-containing ether compound of an embodiment of the present invention is preferably a compound represented by one of formulas (A) to (V) shown below.

The symbols xa to xj and xu in the following formulas (A) to (J) and (U) correspond with q in formula (2). Further, the symbols yk to yt and yv in the following formulas (K) to (T) and (V) correspond with q in formula (2). The repeating numbers xa to xj, xu, yk to yt, and yv in formulas (A) to (V) are numbers that indicate the average degree of polymerization, and therefore are not necessarily integers.

The compounds represented by formulas (A) to (C), (H) to (M), (R) to (T), (U) and (V) shown below are all compounds of the formula (1) in which $R^3$ and $R^1$ are different terminal groups. Further, the compounds of formulas (D) to (G) and (N) to (Q) shown below are compounds of the formula (1) in which $R^3$ and $R^1$ are identical terminal groups.

In each of the compounds represented by formulas (A) to (C), (H) to (M), and (R) to (T) shown below, $R^1$ is represented by formula (3), and the value of n in formula (3) is 1. In each of the compounds represented by formulas (U) and (V) shown below, $R^1$ is represented by formula (3), and the value of n in formula (3) is 2. Further, in each of the compounds represented by formulas (A) and (K), $R^3$ represents a hydroxyl group. In each of the compounds represented by formulas (B) and (L), $R^3$ is represented by formula (4-1). In each of the compounds represented by formulas (C), (H) to (J), (M), (R) to (T), (U) and (V), $R^3$ is represented by formula (4-2).

In each of the compounds represented by formulas (A) to (C), (H) to (J), and (U) shown below, the value of p in $R^2$ is 3. In each of the compounds represented by formulas (K) to (M), (R) to (T), and (V) shown below, the value of p in $R^2$ is 2.

In each of the compounds represented by formulas (D) and (N) shown below, $R^1$ and $R^3$ are both represented by formula (3), and the value of n in formula (3) is 1. In each of the compounds represented by formulas (E) and (O) shown below, $R^1$ and $R^3$ are both represented by formula (3), and the value of n in formula (3) is 2. In each of the compounds represented by formulas (F) and (P) shown below, $R^1$ and $R^3$ are both represented by formula (3), and the value of n in formula (3) is 3. In each of the compounds represented by formulas (G) and (Q) shown below, $R^1$ and $R^3$ are both represented by formula (3), and the value of n in formula (3) is 4.

In each of the compounds represented by formulas (D) to (G) shown below, the value of p in $R^2$ is 3. In each of the compounds represented by formulas (N) to (Q) shown below, the value of p in $R^2$ is 2.

[Chemical formula 7]

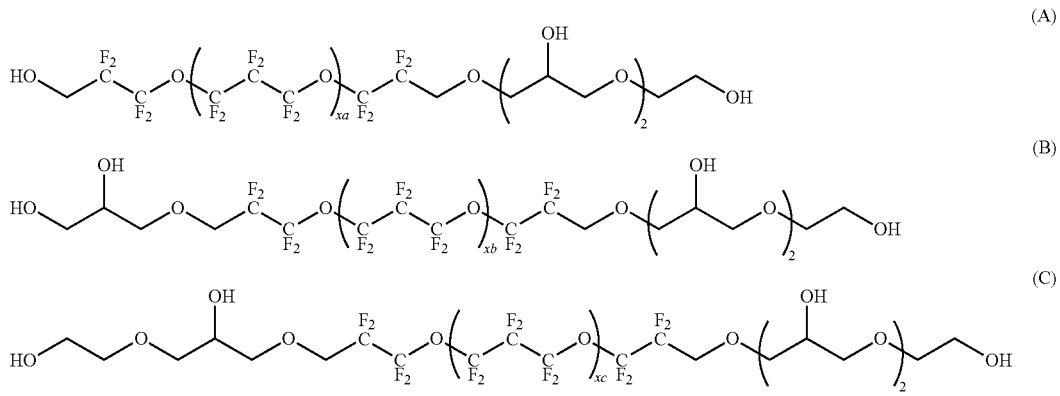

(In formula (A), xa indicates the average polymerization degree, and represents a number from 1 to 14.)
(In formula (B), xb indicates the average polymerization degree, and represents a number from 1 to 14.)
(In formula (C), xc indicates the average polymerization degree, and represents a number from 1 to 14.)

[Chemical formula 8]

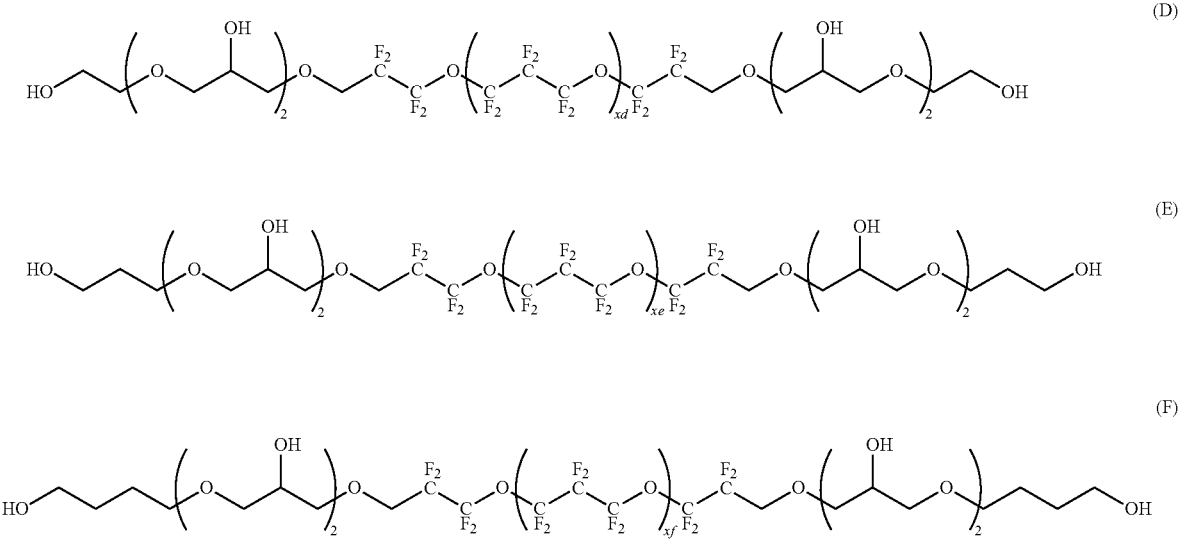

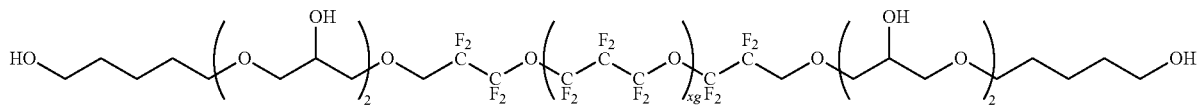
(G)

(In formula (D), xd indicates the average polymerization degree, and represents a number from 1 to 14.)
(In formula (E), xe indicates the average polymerization degree, and represents a number from 1 to 14.)
(In formula (F), xf indicates the average polymerization degree, and represents a number from 1 to 14.)
(In formula (G), xg indicates the average polymerization degree, and represents a number from 1 to 14.)
(In formula (H), xh indicates the average polymerization degree, and represents a number from 1 to 14.)
(In formula (I), xi indicates the average polymerization degree, and represents a number from 1 to 14.)
(In formula (J), xj indicates the average polymerization degree, and represents a number from 1 to 14.)
(In formula (U), xu indicates the average polymerization degree, and represents a number from 1 to 14.)

[Chemical formula 9]

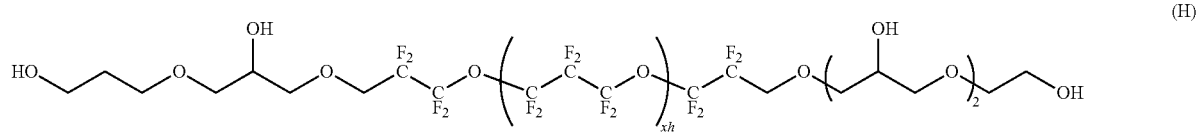
(H)

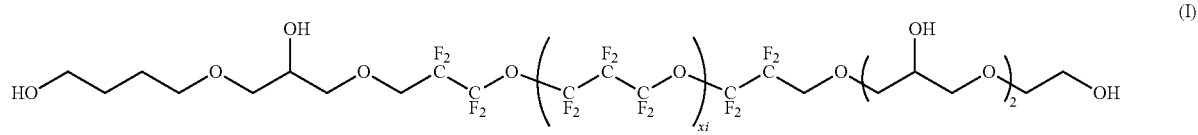
(I)

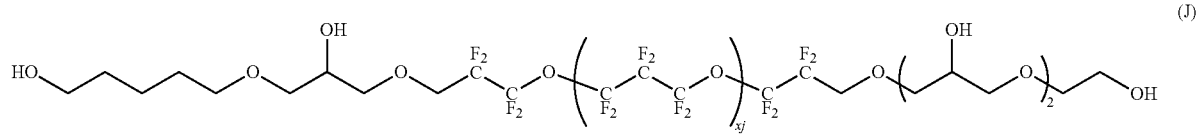
(J)

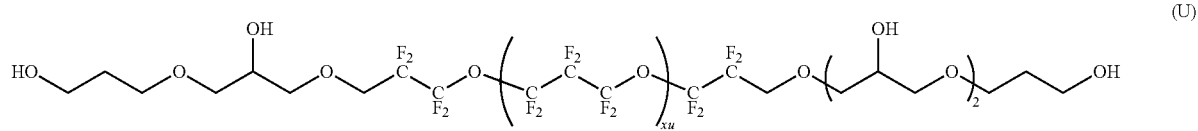
(U)

[Chemical formula 10]

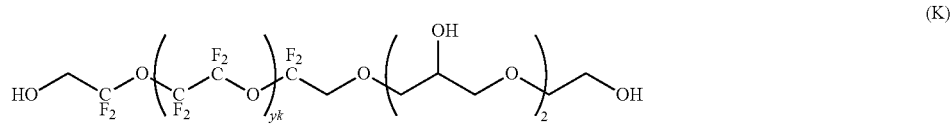
(K)

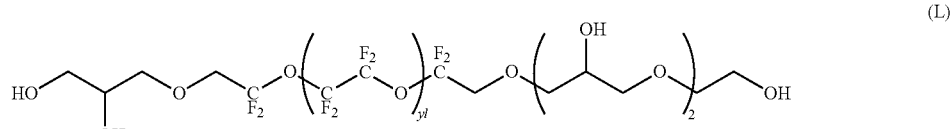
(L)

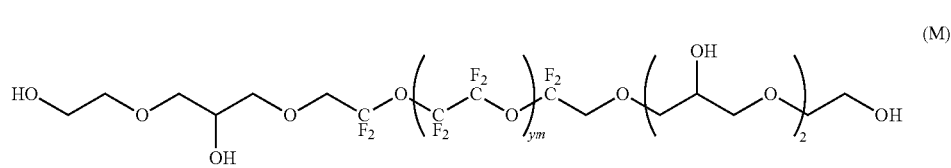
(M)

(In formula (K), yk indicates the average polymerization degree, and represents a number from 1 to 20.)
(In formula (L), yl indicates the average polymerization degree, and represents a number from 1 to 20.)
(In formula (M), ym indicates the average polymerization degree, and represents a number from 1 to 20.)

[Chemical formula 11]

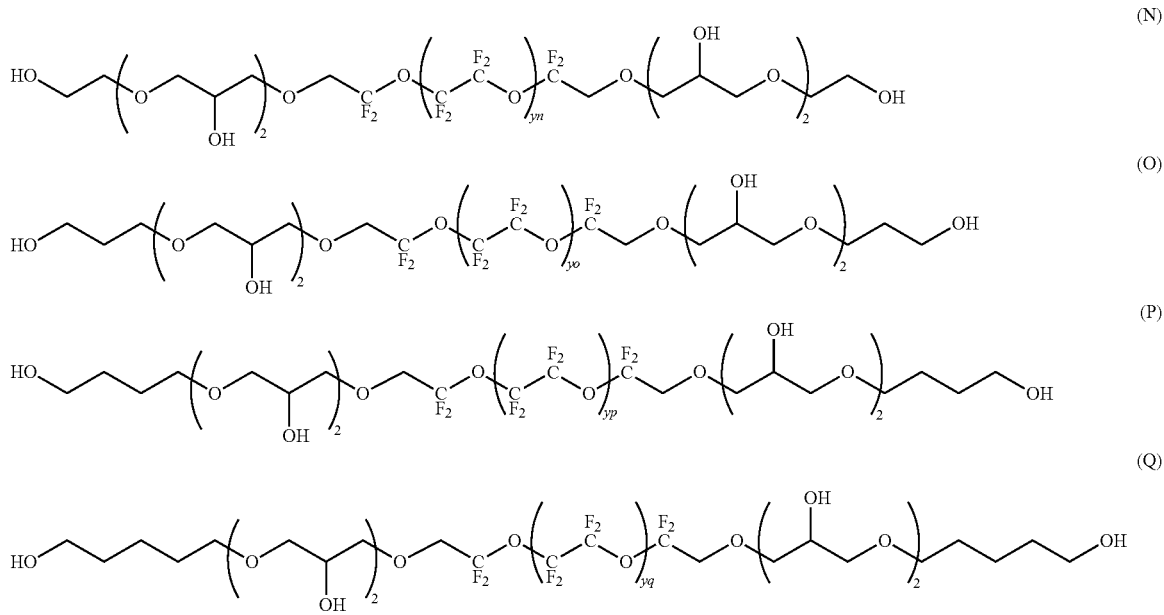

(In formula (N), yn indicates the average polymerization degree, and represents a number from 1 to 20.)
(In formula (O), yo indicates the average polymerization degree, and represents a number from 1 to 20.)
(In formula (P), yp indicates the average polymerization degree, and represents a number from 1 to 20.)
(In formula (Q), yq indicates the average polymerization degree, and represents a number from 1 to 20.)

[Chemical formula 12]

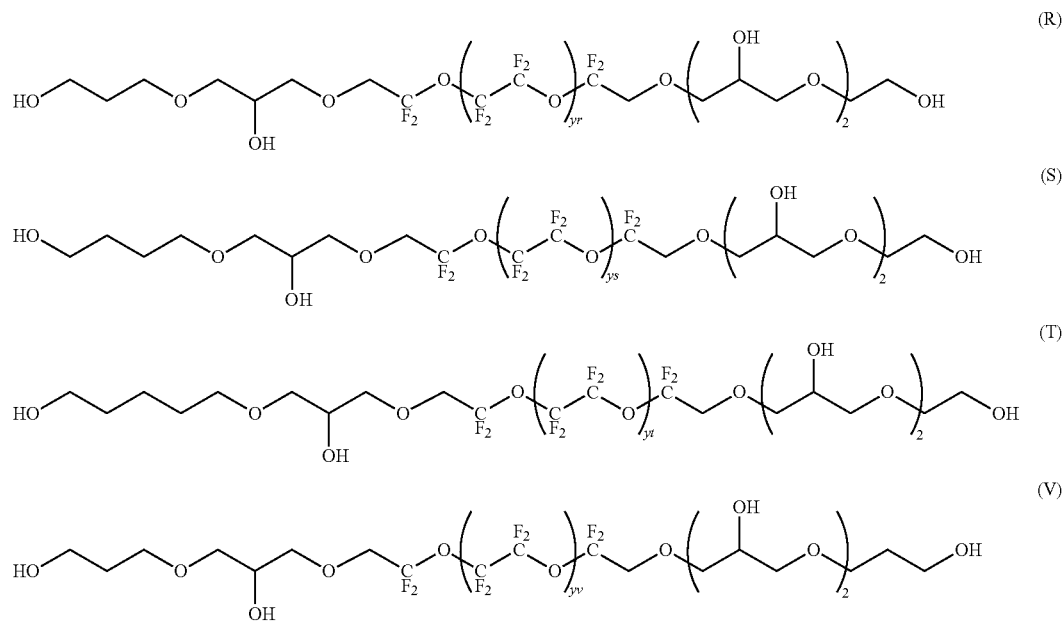

(In formula (R), yr indicates the average polymerization degree, and represents a number from 1 to 20.)
(In formula (S), ys indicates the average polymerization degree, and represents a number from 1 to 20.)
(In formula (T), yt indicates the average polymerization degree, and represents a number from 1 to 20.)
(In formula (V), yv indicates the average polymerization degree, and represents a number from 1 to 20.)

In those cases where the fluorine-containing ether compound represented by formula (1) is a compound represented by one of formulas (A) to (V), a lubricant layer can be obtained which exhibits even better adhesion with the protective layer and better suppression of pickup, as well as excellent chemical substance resistance, and therefore such compounds are preferred.

Among the fluorine-containing ether compounds represented by formula (A) to (V), fluorine-containing ether compounds represented by formulas (C), (D), (E), (M), (N) and (O) are able to form lubricant layers having particularly good adhesion to the protective layer, and are consequently preferred.

The fluorine-containing ether compound of an embodiment of the present invention preferably has a number average molecular weight within a range from 400 to 3,000. When the number average molecular weight is at least 400, a lubricant containing the fluorine-containing ether compound of this embodiment is less likely to vaporize, meaning vaporization and subsequent transfer of the lubricant to the magnetic head can be prevented. The number average molecular weight of the fluorine-containing ether compound is more preferably 800 or greater. Further, when the number average molecular weight is not more than 3,000, the viscosity of the fluorine-containing ether compound is appropriate, and application of a lubricant containing this compound is able to readily form a lubricant layer having the thin thickness. The number average molecular weight of the fluorine-containing ether compound is more preferably 2,500 or less.

The number average molecular weight (Mn) of the fluorine-containing ether compound refers to a value measured by $^1$H-NMR and $^{19}$F-NMR using an AVANCE III 400 device manufactured by Bruker BioSpin Corporation. Specifically, the number of repeating units in the PFPE chain is calculated based on the integral value measured by $^{19}$F-NMR, enabling the number average molecular weight to be determined. The number of repeating units represents an average value, and is therefore sometimes represented with numbers after the decimal point. In the NMR (nuclear magnetic resonance) measurement, the sample was diluted with a hexafluorobenzene/d-acetone (4/1 v/v) solvent prior to measurement. The standard used for the $^{19}$F-NMR chemical shift was the hexafluorobenzene peak at −164.7 ppm, whereas the standard used for the $^1$H-NMR chemical shift was the acetone peak at 2.2 ppm.

[Production Method]

There are no particular limitations on the method used for producing the fluorine-containing ether compound of an embodiment of the present invention, and production may be conducted using conventional production methods. For example, the fluorine-containing ether compound of an embodiment of the present invention may be produced using the production method described below.

First, a fluorine-based compound is prepared that has hydroxymethyl groups (—CH$_2$OH) at both terminals of a perfluoropolyether chain that corresponds with R$^2$ in formula (1). Next, the hydroxyl group of the hydroxymethyl group at each of the terminals (or one of the terminals) of the fluorine-based compound is substituted using a compound having an organic terminal group formed from R$^1$ in formula (1).

In the case where a fluorine-containing ether compound represented by formula (1) in which R$^3$ is a hydroxyl group is produced as the fluorine-containing ether compound, in the substitution reaction described above, the compound having an organic terminal group formed from R$^1$ is used in an amount of approximately 0.5 to 1 equivalents relative to the perfluoropolyether chain. Further, in the case where a fluorine-containing ether compound represented by formula (1) in which R$^3$ is an identical terminal group to R$^1$ is produced as the fluorine-containing ether compound, in the substitution reaction described above, the compound having an organic terminal group formed from R$^1$ is used in an amount of approximately 2 equivalents relative to the perfluoropolyether chain.

When R$^3$ is an identical terminal group to R$^1$ in the fluorine-containing ether compound represented by formula (1), the compound can be produced more easily, and is therefore preferred.

In the case where a fluorine-containing ether compound represented by formula (1) in which R$^3$ is a different terminal group from R$^1$ is produced as the fluorine-containing ether compound, the substitution reaction described above is conducted using the compound having an organic terminal group formed from R$^1$ in an amount of approximately 0.5 to 1 equivalents relative to the perfluoropolyether chain, and subsequently, the hydroxyl group of the hydroxymethyl group located at the terminal of the fluorine-based compound that has not been substituted with the organic terminal group formed from R$^1$ is then substituted using a compound having a terminal group formed from R$^3$ in formula (1). The fluorine-containing ether compound represented by formula (1) in which R$^3$ is a different terminal group from R$^1$ includes compounds in which R$^1$ and R$^3$ are both terminal groups represented by formula (3), but in which the value for n differs in R$^1$ and R$^3$.

In the case of producing a fluorine-containing ether compound in which R$^3$ is a different terminal group from R$^1$ in the formula (1), either the substitution reaction of a hydroxymethyl group of the perfluoropolyether chain with the organic terminal group formed from R$^1$, or the substitution reaction of a hydroxymethyl group of the perfluoropolyether chain with the terminal group formed from R$^3$, may be conducted first.

These substitution reactions may be conducted using conventional methods, and the methods may be determined appropriately in accordance with the types of the groups R$^1$ and R$^3$ in formula (1).

The fluorine-containing ether compound of an embodiment of the present invention is a compound represented by formula (1) shown above. Accordingly, when a lubricant layer is formed on a protective layer using a lubricant containing this compound, the surface of the protective layer is coated with the PFPE chain represented by R$^2$ in formula (1), and frictional force between the magnetic head and the protective layer is reduced. Further, in a lubricant layer formed using a lubricant containing the fluorine-containing ether compound of this embodiment, due to the existence of the four or more hydroxyl groups in the terminal group represented by R$^1$ located at one terminal of R$^2$ and the terminal group represented by R$^3$ located at the other terminal, the fluorine-containing ether compound is able to adhere strongly to the protective layer, meaning excellent pickup suppression, as well as superior chemical substance resistance, can be achieved.

[Lubricant for Magnetic Recording Medium]

A lubricant for a magnetic recording medium according to an embodiment of the present invention contains the fluorine-containing ether compound represented by formula (1).

The lubricant of this embodiment may be mixed, as required, with conventional materials typically used as lubricant materials, provided that the properties achieved by including the fluorine-containing ether compound represented by formula (1) are not impaired.

Specific examples of these conventional materials include Fomblin (a registered trademark) ZDIAC, Fomblin ZDEAL and Fomblin AM-2001 (all manufactured by Solvay Solexis S.A.), and Moresco A20H (manufactured by Moresco Corporation). Conventional materials that are mixed and used with the lubricant of an embodiment of the present invention preferably have a number average molecular weight of about 400 to 3,000.

In those cases where the lubricant of an embodiment of the present invention contains materials other than the fluorine-containing ether compound represented by formula (1), the amount of the fluorine-containing ether compound represented by formula (1) within the lubricant of the embodiment is preferably at least 50% by mass, and more preferably 70% by mass or greater.

Since the lubricant of this embodiment contains the fluorine-containing ether compound represented by formula (1), the surface of the protective layer can be coated with a high coverage rate, and a lubricant layer having excellent adhesion to the protective layer can be formed even if the thickness is reduced. Further, because the lubricant of this embodiment contains the fluorine-containing ether compound represented by formula (1), a fluorine-containing ether compound that exists within the lubricant layer without adhering (adsorbing) to the protective layer is unlikely to aggregate. Accordingly, aggregation and adhesion of the fluorine-containing ether compound to the magnetic head as foreign matter (smear) can be prevented.

[Magnetic Recording Medium]

The FIGURE is a schematic cross-sectional view illustrating one embodiment of the magnetic recording medium of the present invention.

The magnetic recording medium 10 of this embodiment has a structure in which an adhesive layer 12, a soft magnetic layer 13, a first base layer 14, a second base layer 15, a magnetic layer 16, a protective layer 17, and a lubricant layer 18 are provided in sequence on a substrate 11.

[Substrate]

Examples of materials that may be used as the substrate 11 include non-magnetic substrates having a film composed of NiP or a NiP alloy formed on a substrate composed of a metal or an alloy material such as Al or an Al alloy. Further, non-magnetic substrates formed from non-metal materials such as glass, ceramic, silicon, silicon carbide, carbon or resin may also be used as the substrate 11, and non-magnetic substrates having a film composed of NiP or a NiP alloy formed on a substrate formed from one of these non-metal materials may also be used.

[Adhesive Layer]

The adhesive layer 12 prevents progression of corrosion of the substrate 11 when the substrate 11 is positioned in contact with the soft magnetic layer 13 that is provided on top of the adhesive layer 12. The material for the adhesive layer 12 may be selected appropriately from among Cr, Cr alloys, Ti, and Ti alloys and the like. The adhesive layer 12 can be formed, for example, by a sputtering method.

[Soft Magnetic Layer]

The soft magnetic layer 13 preferably has a structure in which a first soft magnetic film, an intermediate layer formed from a Ru film, and a second soft magnetic film are stacked sequentially. In other words, the soft magnetic layer 13 preferably has a structure in which, by sandwiching an intermediate layer formed from a Ru film between two layers of soft magnetic films, the soft magnetic films above and below the intermediate layer are linked by antiferromagnetic coupling (AFC). When the soft magnetic layer 13 has an AFC-coupled structure, the resistance to externally applied magnetic fields, and the resistance to the WATER (Wide Area Track Erasure) phenomenon, which is a characteristic problem of perpendicular magnetic recording, can both be enhanced.

The first soft magnetic film and the second soft magnetic film are preferably films formed from a CoFe alloy. When the first soft magnetic film and the second soft magnetic film are films formed from a CoFe alloy, a high saturation magnetic flux density Bs (of at least 1.4 (T)) can be realized.

One of Zr, Ta and Nb is preferably added to the CoFe alloy used in forming the first soft magnetic film and the second soft magnetic film. This promotes the amorphization of the first soft magnetic film and the second soft magnetic film, enables the orientation of the first base layer (seed layer) to be improved, and also enables a reduction in the floating height of the magnetic head.

The soft magnetic layer 13 can be formed, for example, by a sputtering method.

[First Base Layer]

The first base layer 14 is a layer for controlling the orientation and crystal size of the second base layer 15 and the magnetic layer 16 provided on top of the first base layer 14.

Examples of the first base layer 14 include a Cr layer, Ta layer, Ru layer, or a CrMo, CoW, CrW, CrV or CrTi alloy layer.

The first base layer 14 can be formed, for example, by a sputtering method.

[Second Base Layer]

The second base layer 15 is a layer that controls the orientation of the magnetic layer 16 to achieve a more favorable orientation. The second base layer 15 is preferably a layer formed from Ru or a Ru alloy.

The second base layer 15 may be composed of a single layer, or may be composed of a plurality of layers. When the second base layer 15 is composed of a plurality of layers, all of the layers may be formed from the same material, or at least one layer may be formed from a different material.

The second base layer 15 can be formed, for example, by a sputtering method.

[Magnetic Layer]

The magnetic layer 16 is formed from a magnetic film having an easy axis of magnetization that is oriented in either the perpendicular direction or the horizontal direction relative to the substrate surface. The magnetic layer 16 is a layer containing Co and Pt, and may also contain oxides, or Cr, B, Cu, Ta or Zr or the like in order to improve the SNR characteristics.

Examples of oxides that may be included in the magnetic layer 16 include $SiO_2$, $SiO$, $Cr_2O_3$, $CoO$, $Ta_2O_3$ and $TiO_2$.

The magnetic layer 16 may be composed of a single layer, or may be composed of a plurality of magnetic layers formed from materials having different compositions.

For example, in the case where the magnetic layer 16 is composed of three layers, consisting of a first magnetic layer, a second magnetic layer and a third magnetic layer stacked in that order from the lower side, the first magnetic layer preferably has a granular structure formed from a material containing Co, Cr and Pt, and also containing oxides. Examples of preferred oxides that may be included in the first magnetic layer include oxides of Cr, Si, Ta, Al, Ti, Mg and Co. Among these, oxides such as $TiO_2$, $Cr_2O_3$ and $SiO_2$ can be used particularly favorably. Further, the first magnetic layer is preferably formed from a composite oxide containing two or more added oxides. Among such composite oxides, $Cr_2O_3$—$SiO_2$, $Cr_2O_3$—$TiO_2$, and $SiO_2$—$TiO_2$ and the like can be used particularly favorably.

The first magnetic layer may also contain, in addition to Co, Cr, Pt and the oxides, one or more elements selected from among B, Ta, Mo, Cu, Nd, W, Nb, Sm, Tb, Ru and Re. The same materials as those used for the first magnetic layer can be used for the second magnetic layer. The second magnetic layer preferably has a granular structure.

The third magnetic layer preferably has a non-granular structure formed from a material containing Co, Cr and Pt, but containing no oxides. In addition to Co, Cr and Pt, the third magnetic layer may also contain one or more elements selected from among B, Ta, Mo, Cu, Nd, W, Nb, Sm, Tb, Ru, Re and Mn.

In those cases where the magnetic layer 16 is formed from a plurality of magnetic layers, a non-magnetic layer is preferably provided between adjacent magnetic layers. When the magnetic layer 16 is composed of three layers, namely a first magnetic layer, a second magnetic layer and a third magnetic layer, a non-magnetic layer is preferably provided between the first magnetic layer and the second magnetic layer, and between the second magnetic layer and the third magnetic layer.

Examples of materials that may be used favorably for the non-magnetic layers provided between the adjacent magnetic layers of the magnetic layer 16 include Ru, Ru alloys, CoCr alloys, and CoCrX1 alloys (wherein X1 represents one element, or two or more elements, selected from among Pt, Ta, Zr, Re, Ru, Cu, Nb, Ni, Mn, Ge, Si, O, N, W, Mo, Ti, V and B) and the like.

Alloy materials containing oxides, metal nitrides or metal carbides are preferably used for the non-magnetic layers provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$ and $TiO_2$. Examples of metal nitrides that may be used include AlN, $Si_3N_4$, TaN and CrN. Examples of metal carbides that may be used include TaC, BC and SiC.

The non-magnetic layers may be formed, for example, by a sputtering method.

In order to achieve a higher recording density, the magnetic layer 16 is preferably a magnetic layer for perpendicular magnetic recording in which the easy axis of magnetization is oriented in a direction perpendicular to the substrate surface. However, a magnetic layer for in-plane magnetic recording may also be used for the magnetic layer 16.

The magnetic layer 16 may be formed using any conventional method such as a vapor deposition method, ion beam sputtering method or magnetron sputtering method. The magnetic layer 16 is usually formed by a sputtering method.

[Protective Layer]

The protective layer 17 protects the magnetic layer 16. The protective layer 17 may be composed of a single layer, or may be composed of a plurality of layers. Examples of the material for the protective layer 17 include carbon, carbon which contains nitrogen, and silicon carbide.

A carbon-based protective layer can be used favorably as the protective layer 17, and an amorphous carbon protective layer is particularly preferred. When the protective layer 17 is a carbon-based protective layer, the interactions with the polar groups (and particularly the hydroxyl groups) contained in the fluorine-containing ether compound included in the lubricant layer 18 can be further enhanced, which is desirable.

The adhesive strength between the carbon-based protective layer and the lubricant layer 18 can be controlled by using a hydrogenated carbon and/or nitrogenated carbon for the carbon-based protective layer, and then adjusting the hydrogen content and/or nitrogen content in the carbon-based protective layer. The hydrogen content in the carbon-based protective layer, when measured by hydrogen front scattering (HFS), is preferably within a range from 3 to 20 atomic %. Further, the nitrogen content in the carbon-based protective layer, when measured by X-ray photoelectron spectroscopy (XPS), is preferably within a range from 4 to 15 atomic %.

The hydrogen and/or nitrogen contained in the carbon-based protective layer is not necessarily distributed uniformly through the entire carbon-based protective layer. For example, the carbon-based protective layer preferably is a composition gradient layer in which the nitrogen is incorporated on the lubricant layer 18 side in the protective layer 17 and the hydrogen is incorporated on the magnetic layer 16 side in the protective layer 17. In this case, the adhesive strength between the carbon-based protective layer and the magnetic layer 16 and lubricant layer 18 can be further improved.

The thickness of the protective layer 17 is preferably within a range from 1 nm to 7 nm. When the thickness of the protective layer 17 is at least 1 nm, satisfactory performance as the protective layer 17 can be achieved. When the thickness of the protective layer 17 is not more than 7 nm, it is preferable from the viewpoint of keeping the protective layer 17 thin.

Examples of the method used for depositing the protective layer 17 include sputtering methods using a target material containing carbon, CVD (chemical vapor deposition) methods using a hydrocarbon raw material such as ethylene or toluene, and IBD (ion beam deposition) methods.

In those cases where a carbon-based protective layer is formed as the protective layer 17, the protective layer can be deposited, for example, using a DC magnetron sputtering method. In particular, when forming a carbon-based protective layer as the protective layer 17, deposition of an amorphous carbon protective layer using a plasma CVD method is preferred. An amorphous carbon protective layer deposited by a plasma CVD method has a uniform surface with very little roughness.

[Lubricant Layer]

The lubricant layer 18 prevents contamination of the magnetic recording medium 10. Further, the lubricant layer 18 also reduces the frictional force of the magnetic head of the magnetic recording and playback device that slides across the top of the magnetic recording medium 10, and improves the durability of the magnetic recording medium 10.

As illustrated in the FIGURE, the lubricant layer 18 is formed so as to contact the protective layer 17. The lubricant layer 18 contains the fluorine-containing ether compound of an embodiment of the present invention.

In those cases where the protective layer 17 disposed beneath the lubricant layer 18 is a carbon-based protective layer, the lubricant layer 18 bonds to the protective layer 17 with a particularly powerful bonding strength. As a result, even if the thickness of the lubricant layer 18 is reduced, a magnetic recording medium 10 in which the surface of the protective layer 17 is coated with a high coverage rate can be obtained easily, and contamination of the surface of the magnetic recording medium 10 can be effectively prevented.

The average thickness of the lubricant layer 18 is preferably within a range from 0.5 nm (5 Å) to 1.5 nm (15 Å), and more preferably from 0.6 nm (6 Å) to 1.1 nm (11 Å). When the average thickness of the lubricant layer 18 is at least 0.5 nm, the lubricant layer 18 is formed with uniform thickness without becoming an island-like or mesh-like layer. As a result, the surface of the protective layer 17 can be coated with the lubricant layer 18 with a high coverage rate. Further, when the average thickness of the lubricant layer 18 is not more than 1.5 nm, the lubricant layer 18 can be kept suitably thin, and the floating height of the magnetic head can be satisfactorily reduced.

When the surface of the protective layer 17 is not coated with the lubricant layer 18 with a satisfactorily high coverage rate, environmental substances adsorbed to the surface of the magnetic recording medium 10 can pass through voids in the lubricant layer 18 and penetrate beneath the lubricant layer 18. Environmental substances that penetrate beneath the lubricant layer 18 can adsorb and bond to the protective layer 17, producing contaminants. Then, during magnetic recording or playback, these contaminants (aggregated components) can adhere (transfer) to the magnetic head as smear, and may cause damage to the magnetic head, or cause a deterioration in the magnetic recording and playback characteristics of the magnetic recording and playback device.

Examples of environmental substances that produce contaminants include siloxane compounds (cyclic siloxanes and linear siloxanes), ionic impurities, hydrocarbons having comparatively large molecular weights such as octacosane, and plasticizers such as dioctyl phthalate. Examples of metal ions that may be incorporated in the ionic impurities include sodium ions and potassium ions. Examples of inorganic ions that may be incorporated in the ionic impurities include chloride ions, bromide ions, nitrate ions, sulfate ions and ammonium ions. Examples of organic ions that may be incorporated in the ionic impurities include oxalate ions and formate ions.

[Lubricant Layer Formation Method]

One example of the method used for forming the lubricant layer 18 is a method in which a partially produced magnetic recording medium is first prepared having each of the layers up to and including the protective layer 17 formed on the substrate 11, and a solution for forming the lubricant layer is then applied to the protective layer 17 and dried.

The solution for forming the lubricant layer is obtained, for example, by dispersing or dissolving the magnetic recording medium lubricant of the embodiment described above in a solvent as required, so as to achieve a viscosity and concentration that are suitable for the coating method being used.

Examples of the solvent used in the solution for forming the lubricant layer include fluorine-based solvents such as Vertrel (a registered trademark) XF (a product name, manufactured by Mitsui DuPont Fluorochemicals Co., Ltd.) and the like.

There are no particular limitations on the coating method used for applying the solution for forming the lubricant layer, and examples include spin-coating methods, spray methods, paper coating methods, and dipping methods.

When a dipping method is used, for example, the method described below may be employed. First, the substrate 11 having the various layers up to and including the protective layer 17 formed thereon is dipped in the solution for forming the lubricant layer housed in the dipping tank of a dip coating device. Subsequently, the substrate 11 is pulled up out of the dipping tank at a prescribed speed. This coats the solution for forming the lubricant layer onto the surface of the protective layer 17 of the substrate 11.

By using a dipping method, the solution for forming the lubricant layer can be applied uniformly to the surface of the protective layer 17, enabling the lubricant layer 18 to be formed with a uniform thickness on the protective layer 17.

In an embodiment of the present invention, the substrate 11 having the lubricant layer 18 formed thereon is preferably subjected to a heat treatment. Conducting a heat treatment improves the adhesion between the lubricant layer 18 and the protective layer 17, and increases the adhesive strength between the lubricant layer 18 and the protective layer 17.

The heat treatment temperature is preferably within a range from 90 to 180° C. When the heat treatment temperature is at least 90° C., a satisfactory improvement in the adhesion between the lubricant layer 18 and the protective layer 17 can be achieved. Further, when the heat treatment temperature is not more than 180° C., thermal degradation of the lubricant layer 18 can be prevented. The heat treatment time is preferably within a range from 10 to 120 minutes.

The magnetic recording medium 10 of an embodiment of the present invention has at least the magnetic layer 16, the protective layer 17 and the lubricant layer 18 provided sequentially on the substrate 11. In the magnetic recording medium 10 of this embodiment, the lubricant layer 18 containing the fluorine-containing ether compound of an embodiment of the present invention is formed so as to contact the protective layer 17. Even if the thickness of this lubricant layer 18 is reduced, the surface of the protective layer 17 can be coated with a high coverage rate. Consequently, in the magnetic recording medium 10 of this embodiment, the problem of environmental substances that can produce contaminants such as ionic impurities penetrating through voids in the lubricant layer 18 can be prevented. Accordingly, the magnetic recording medium 10 of this embodiment is a medium in which few contaminants exist on the surface. Further, the lubricant layer 18 in the magnetic recording medium 10 of this embodiment is less likely to generate foreign matter (smear), and can suppress pickup. As a result, the magnetic recording medium 10 of an embodiment of the present invention has excellent reliability and durability.

EXAMPLES

The present invention is described below in further detail using a series of examples and comparative examples. However, the present invention is not limited solely to the following examples.

Example 1

A compound represented by formula (A) shown below was produced using the method described below.

Under a nitrogen gas atmosphere, a 100 mL round-bottom flask was charged with 22.2 g (20 mmol) of a compound represented by $HOCH_2CF_2CF_2O(CF_2CF_2CF_2O)_xCF_2CF_2CH_2OH$ (wherein x in the formula is 5.0) (number average molecular weight: 1,108, molecular weight distribution: 1.1), 3.84 g (12 mmol) of a compound represented by formula (7) shown below and 18 mL of t-butanol, and the contents were stirred at room temperature until a uniform mixture was obtained. Subsequently, 0.674 g (6.0 mmol) of potassium tert-butoxide was added to the uniform liquid, and the resulting mixture was reacted under stirring at 70° C. for 10 hours and then left to cool to room temperature. Subsequently, 40 mL of a 10% hydrogen chloride methanol solution (product name: X0041, hydrogen chloride-methanol reagent (5 to 10%) manufactured by Tokyo Chemical Industry Co., Ltd.) was added to the reaction liquid, and the resulting mixture was stirred at room temperature for 2 hours, thereby deprotecting the methoxymethyl (MOM) group and tetrahydropyranyl (THP) group that are the protective groups derived from the compound of formula (7). A 5% sodium bicarbonate solution was added to the obtained reaction liquid until the pH of the reaction liquid became alkaline, and then 20 mL of water was added. This reaction liquid was then extracted twice with 100 mL portions of ethyl acetate. The organic phase obtained from the extraction was washed with water, and then dried over anhydrous sodium sulfate. Following removal of the desiccant by filtration, the filtrate was concentrated, and the residue was purified by silica gel column chromatography, yielding 10.42 g of a compound (A) represented by formula (A) shown below.

The compound represented by formula (7) was synthesized using the method described below. Following protection of the primary hydroxyl group of a commercially available 3-allyloxy-1,2-propanediol with a tert-butyldimethylsilyl (TBS) group, the secondary hydroxyl group was protected with a methoxymethyl group. Subsequently, following deprotection of the TBS group from the compound, the resulting primary hydroxyl group was reacted with 2-(2-bromoethoxy)tetrahydro-2H-pyran, and then oxidized. The above steps yielded the compound represented by formula (7).

[Chemical formula 13]

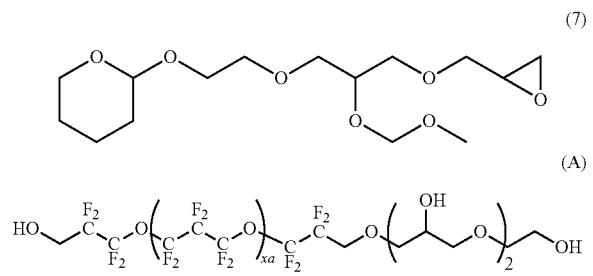

(In formula (A), xa represents 5.0.)

A $^1$H-NMR measurement of the obtained compound (A) was conducted, and the structure was identified based on the following results.

Compound (A): $^1$H-NMR (CD$_3$COCD$_3$): δ [ppm]3.4 to 4.2 (22H)

Example 2

Following reaction in the same manner as Example 1, 50 mL of water was added to the obtained reaction liquid without adding the 10% hydrogen chloride methanol solution (product name: X0041, hydrogen chloride-methanol reagent (5 to 10%) manufactured by Tokyo Chemical Industry Co., Ltd.), and the resulting mixture was extracted twice with 100 mL portions of ethyl acetate. The organic phase obtained from the extraction was washed with water, and then dried over anhydrous sodium sulfate. Following removal of the desiccant by filtration, the filtrate was concentrated, and the residue was purified by silica gel column chromatography, yielding 11.45 g of a compound represented by formula (21) shown below.

[Chemical formula 14]

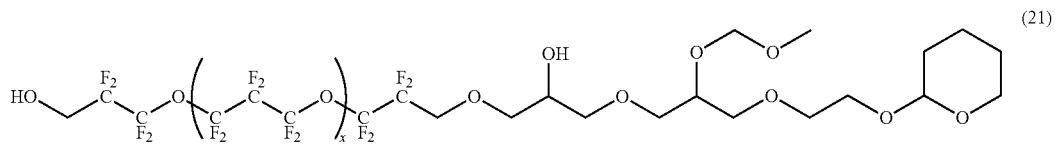

(In formula (21), x represents 5.0.)

A flask was charged with 11.43 g (8.0 mmol) of the compound represented by formula (21), 1.27 g (8.0 mmol) of a compound represented by formula (8) shown below and 22 mL of t-butanol, and the contents were stirred at room temperature until a uniform mixture was obtained. Subsequently, 0.135 g (1.2 mmol) of potassium tert-butoxide was added to the uniform liquid, and the resulting mixture was reacted under stirring at 70° C. for 120 hours and then left to cool to room temperature. Subsequently, 20 mL of a 10% hydrogen chloride methanol solution (product name: X0041, hydrogen chloride-methanol reagent (5 to 10%) manufactured by Tokyo Chemical Industry Co., Ltd.) was added to the reaction liquid, and the resulting mixture was stirred at room temperature for 2 hours, thereby deprotecting the methoxymethyl (MOM) group and tetrahydropyranyl (THP) group that are the protective groups derived from the compound of formula (7). A 5% sodium bicarbonate solution was added to the obtained reaction liquid until the pH of the reaction liquid became alkaline, and then 16 mL of water was added. This reaction liquid was then extracted twice with 100 mL portions of ethyl acetate. The organic phase obtained from the extraction was washed with water, and then dried over anhydrous sodium sulfate. Following removal of the desiccant by filtration, the filtrate was concentrated, and the residue was purified by silica gel column chromatography, yielding 10.42 g of a compound (B) represented by formula (B) shown below.

The compound represented by formula (8) was obtained by oxidizing a commercially available 2-allyloxytetrahydropyran.

[Chemical formula 15]

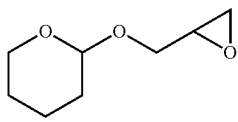

(8)

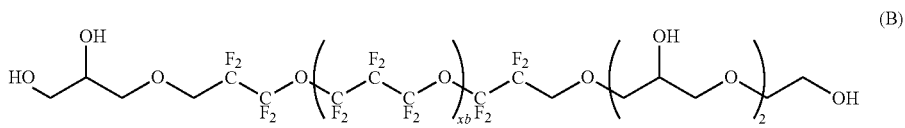

(B)

(In formula (B), xb represents 5.0.)

A $^1$H-NMR measurement of the obtained compound (B) was conducted, and the structure was identified based on the following results.

Compound (B): $^1$H-NMR (CD$_3$COCD$_3$): δ [ppm]3.4 to 4.2 (28H)

Example 3

With the exception of using 1.62 g of a compound represented by formula (9) shown below instead of the compound represented by formula (8), the same operations as Example 2 were conducted, yielding 7.94 g of a compound (C) represented by formula (C) shown below.

The compound represented by formula (9) was synthesized by protecting the hydroxyl group of a commercially available ethylene glycol monoallyl ether with dihydropyran, and then oxidizing the double bond.

[Chemical formula 16]

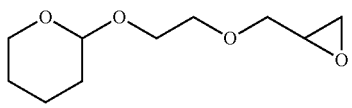

(9)

CF$_2$CF$_2$CH$_2$OH (wherein x in the formula is 5.0) (number average molecular weight: 1,108, molecular weight distribution: 1.1), 6.41 g (20 mmol) of the compound represented by formula (7) and 30 mL of t-butanol, and the contents were stirred at room temperature until a uniform mixture was obtained. Subsequently, 0.168 g (1.5 mmol) of potassium tert-butoxide was added to the uniform liquid, and the resulting mixture was reacted under stirring at 70° C. for 20 hours and then left to cool to room temperature. Subsequently, 40 mL of a 10% hydrogen chloride methanol solution (product name: X0041, hydrogen chloride-methanol reagent (5 to 10%) manufactured by Tokyo Chemical Industry Co., Ltd.) was added to the reaction liquid, and the resulting mixture was stirred at room temperature for 2 hours, thereby deprotecting the methoxymethyl (MOM) group and tetrahydropyranyl (THP) group that are the protective groups derived from the compound of formula (7). A 5% sodium bicarbonate solution was added to the obtained

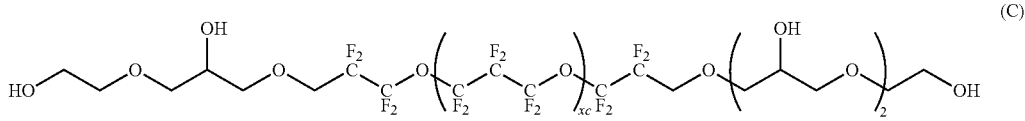

(C)

(In formula (C), xc represents 5.0.)

A $^1$H-NMR measurement of the obtained compound (C) was conducted, and the structure was identified based on the following results.

Compound (C): $^1$H-NMR (CD$_3$COCD$_3$): δ [ppm]3.4 to 4.2 (32H)

Example 4

Under a nitrogen gas atmosphere, a 100 mL round-bottom flask was charged with 11.1 g (10 mmol) of a compound represented by HOCH$_2$CF$_2$CF$_2$O(CF$_2$CF$_2$CF$_2$O)$_x$ reaction liquid until the pH of the reaction liquid became alkaline, and then 20 mL of water was added. This reaction liquid was then extracted twice with 100 mL portions of ethyl acetate. The organic phase obtained from the extraction was washed with water, and then dried over anhydrous sodium sulfate. Following removal of the desiccant by filtration, the filtrate was concentrated, and the residue was purified by silica gel column chromatography, yielding 10.45 g of a compound (D) represented by formula (D) shown below.

[Chemical formula 17]

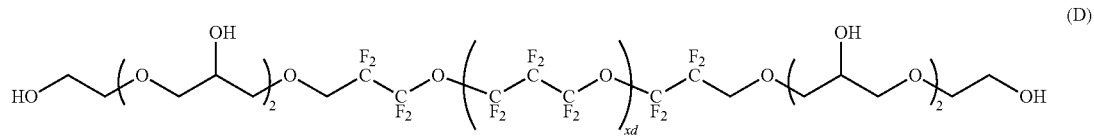

(D)

(In formula (D), xd represents 5.0.)

A $^1$H-NMR measurement of the obtained compound (D) was conducted, and the structure was identified based on the following results.

Compound (D): $^1$H-NMR (CD$_3$COCD$_3$): δ [ppm]3.4 to 4.2 (38H)

Example 5

With the exception of using 6.69 g of a compound represented by formula (10) shown below instead of the compound represented by formula (7), the same operations as Example 4 were conducted, yielding 10.64 g of a compound (E) represented by formula (E) shown below.

The compound represented by formula (10) shown below was synthesized in a similar manner to that described for the compound represented by formula (7), by using 2-(3-bromopropoxy)tetrahydro-2H-pyran.

[Chemical formula 18]

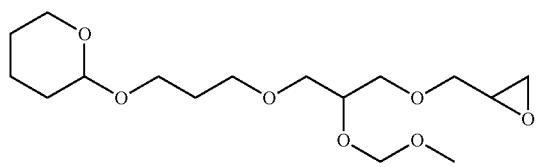

(10)

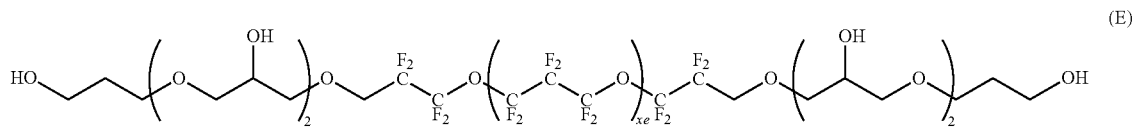

(E)

(In formula (E), xe represents 5.0.)

A $^1$H-NMR measurement of the obtained compound (E) was conducted, and the structure was identified based on the following results.

Compound (E): $^1$H-NMR (CD$_3$COCD$_3$): δ [ppm] 1.6 to 1.8 (4H), 3.4 to 4.2 (38H)

Example 6

With the exception of using 6.97 g of a compound represented by formula (11) shown below instead of the compound represented by formula (7), the same operations as Example 4 were conducted, yielding 10.07 g of a compound (F) represented by formula (F) shown below.

The compound represented by formula (11) shown below was synthesized in a similar manner to that described for the compound represented by formula (7), by using 2-(4-chlorobutoxy)tetrahydropyran.

[Chemical formula 19]

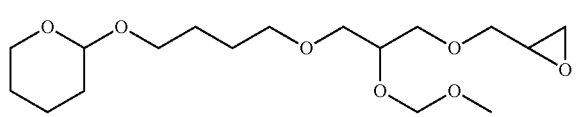

(11)

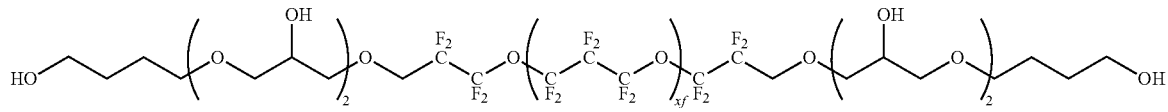

(F)

(In formula (F), xf represents 5.0.)

A ¹H-NMR measurement of the obtained compound (F) was conducted, and the structure was identified based on the following results.

Compound (F): ¹H-NMR (CD$_3$COCD$_3$): δ [ppm] 1.6 to 1.8 (8H), 3.4 to 4.2 (38H)

Example 7

With the exception of using 7.20 g of a compound represented by formula (12) shown below instead of the compound represented by formula (7), the same operations as Example 4 were conducted, yielding 9.46 g of a compound (G) represented by formula (G) shown below.

The compound represented by formula (12) shown below was synthesized in a similar manner to that described for the compound represented by formula (7), by using 2-(5-bromopentyloxy)tetrahydro-2H-pyran derived from 5-bromo-1-pentanol.

[Chemical formula 20]

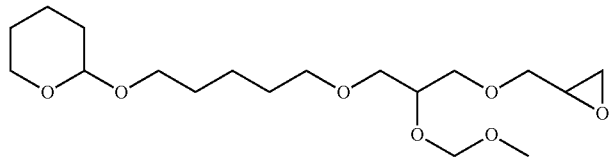

(12)

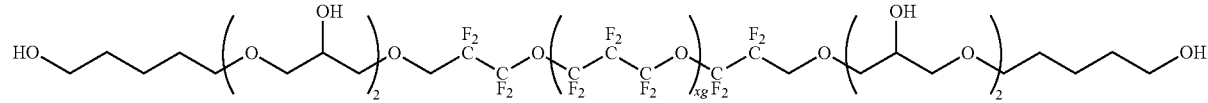

(G)

(In formula (G), xg represents 5.0.)

A ¹H-NMR measurement of the obtained compound (G) was conducted, and the structure was identified based on the following results.

Compound (G): ¹H-NMR (CD$_3$COCD$_3$): δ [ppm] 1.4 to 1.8 (12H), 3.4 to 4.2 (38H)

Example 8

With the exception of using 1.73 g of a compound represented by formula (13) shown below instead of the compound represented by formula (9), the same operations as Example 3 were conducted, yielding 7.68 g of a compound (H) represented by formula (H) shown below.

The compound represented by formula (13) was synthesized from epichlorohydrin and a compound prepared by protecting one hydroxyl group of 1,3-propanediol with THP.

[Chemical formula 21]

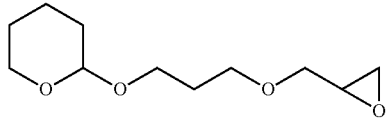

(13)

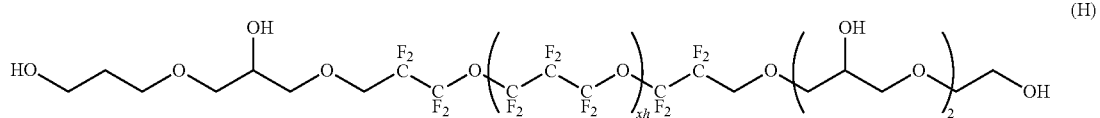

(In formula (H), xh represents 5.0.)

A $^1$H-NMR measurement of the obtained compound (H) was conducted, and the structure was identified based on the following results.

Compound (H): $^1$H-NMR (CD$_3$COCD$_3$): δ [ppm] 1.6 to 1.8 (2H), 3.4 to 4.2 (32H)

Example 9

With the exception of using 1.84 g of a compound represented by formula (14) shown below instead of the compound represented by formula (9), the same operations as Example 3 were conducted, yielding 8.58 g of a compound (1) represented by formula (1) shown below.

The compound represented by formula (14) was synthesized from epichlorohydrin and a compound prepared by protecting one hydroxyl group of 1,4-butanediol with THP.

[Chemical formula 22]

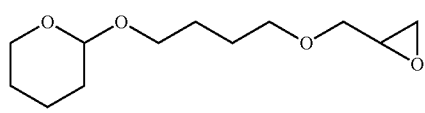

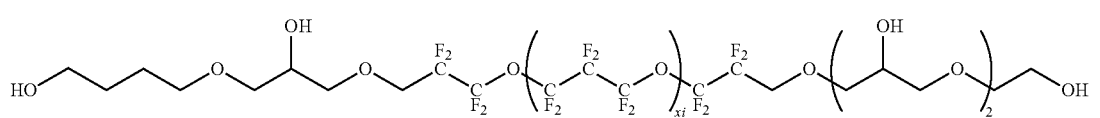

(In formula (I), xi represents 5.0.)

A $^1$H-NMR measurement of the obtained compound (I) was conducted, and the structure was identified based on the following results.

Compound (I): $^1$H-NMR (CD$_3$COCD$_3$): δ [ppm] 1.6 to 1.8 (4H), 3.4 to 4.2 (32H)

Example 10

With the exception of using 1.96 g of a compound represented by formula (15) shown below instead of the compound represented by formula (9), the same operations as Example 3 were conducted, yielding 8.88 g of a compound (J) represented by formula (J) shown below.

The compound represented by formula (15) was synthesized from epichlorohydrin and a compound prepared by protecting one hydroxyl group of 1,5-pentanediol with a tetrahydropyranyl (THP) group.

[Chemical formula 23]

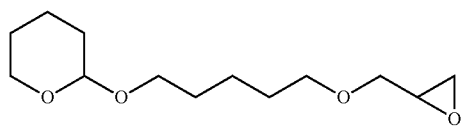

-continued (J)

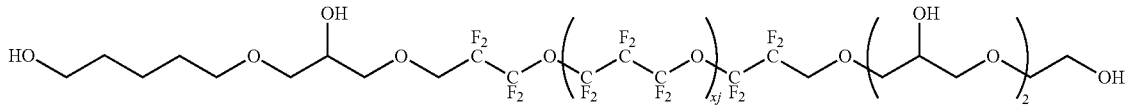

(In formula (J), xj represents 5.0.)

A $^1$H-NMR measurement of the obtained compound (J) was conducted, and the structure was identified based on the following results.

Compound (J): $^1$H-NMR (CD$_3$COCD$_3$): δ [ppm] 1.4 to 1.8 (6H), 3.4 to 4.2 (32H)

Example 11

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 1 were conducted, yielding 9.92 g of a compound (K) represented by formula (K) shown below.

[Chemical formula 25]

[Chemical formula 24]

(K)

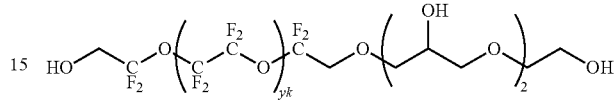

(In formula (K), yk represents 8.0.)

A $^1$H-NMR measurement of the obtained compound (K) was conducted, and the structure was identified based on the following results.

Compound (K): $^1$H-NMR (CD$_3$COCD$_3$): δ [ppm] 3.4 to 4.2 (22H)

Example 12

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 2 were conducted, yielding 7.94 g of a compound (L) represented by formula (L) shown below.

(L)

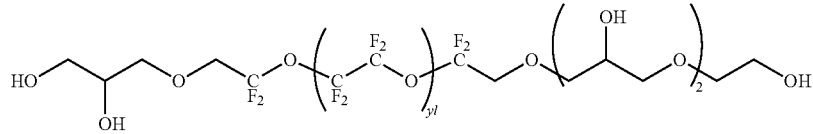

(In formula (L), yl represents 8.0.)

A $^1$H-NMR measurement of the obtained compound (L) was conducted, and the structure was identified based on the following results.

Compound (L): $^1$H-NMR (CD$_3$COCD$_3$): δ [ppm] 3.4 to 4.2 (28H)

Example 13

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 3 were conducted, yielding 8.17 g of a compound (M) represented by formula (M) shown below.

[Chemical formula 26]

(M)

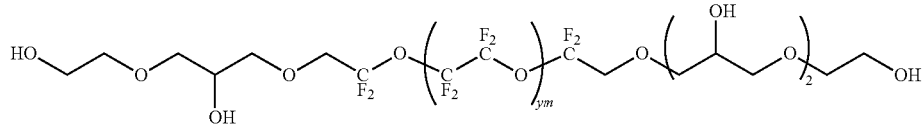

(In formula (M), ym represents 8.0.)

A $^1$H-NMR measurement of the obtained compound (M) was conducted, and the structure was identified based on the following results.

Compound (M): $^1$H-NMR (CD$_3$COCD$_3$): δ [ppm]3.4 to 4.2 (32H)

Example 14

With the exception of using 11.06 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 4 were conducted, yielding 8.89 g of a compound (N) represented by formula (N) shown below.

[Chemical formula 27]

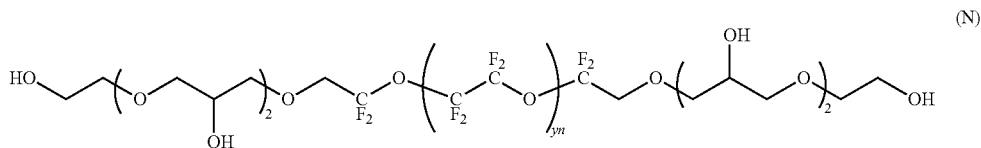

(N)

(In formula (N), yn represents 8.0.)

A $^1$H-NMR measurement of the obtained compound (N) was conducted, and the structure was identified based on the following results.

Compound (N): $^1$H-NMR (CD$_3$COCD$_3$): δ [ppm]3.4 to 4.2 (38H)

Example 15

With the exception of using 11.06 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 5 were conducted, yielding 8.99 g of a compound (O) represented by formula (O) shown below.

[Chemical formula 28]

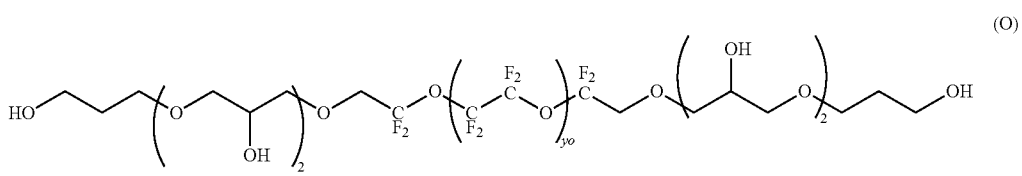

(O)

(In formula (O), yo represents 8.0.)

A $^1$H-NMR measurement of the obtained compound (O) was conducted, and the structure was identified based on the following results.

Compound (O): $^1$H-NMR (CD$_3$COCD$_3$): δ [ppm] 1.6 to 1.8 (4H), 3.4 to 4.2 (38H)

Example 16

With the exception of using 11.06 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 6 were conducted, yielding 9.78 g of a compound (P) represented by formula (P) shown below.

[Chemical formula 29]

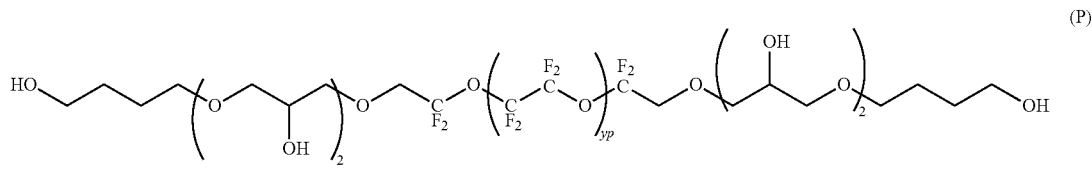
(P)

(In formula (P), yp represents 8.0.)

A $^1$H-NMR measurement of the obtained compound (P) was conducted, and the structure was identified based on the following results.

Compound (P): $^1$H-NMR (CD$_3$COCD$_3$): δ [ppm] 1.6 to 1.8 (8H), 3.4 to 4.2 (38H)

Example 17

With the exception of using 11.06 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 7 were conducted, yielding 9.87 g of a compound (Q) represented by formula (Q) shown below.

[Chemical formula 30]

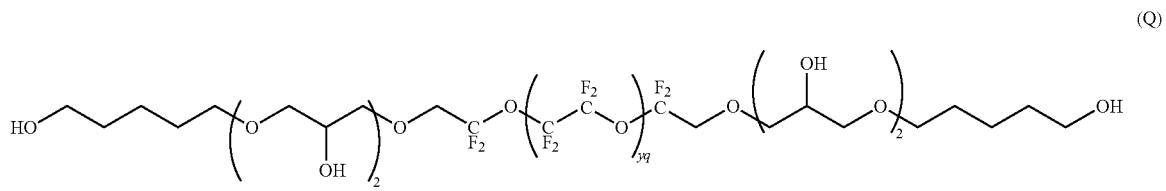
(Q)

(In formula (Q), yq represents 8.0.)

A $^1$H-NMR measurement of the obtained compound (Q) was conducted, and the structure was identified based on the following results.

Compound (Q): $^1$H-NMR (CD$_3$COCD$_3$): δ [ppm] 1.4 to 1.8 (12H), 3.4 to 4.2 (38H)

Example 18

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 8 were conducted, yielding 8.24 g of a compound (R) represented by formula (R) shown below.

[Chemical formula 31]

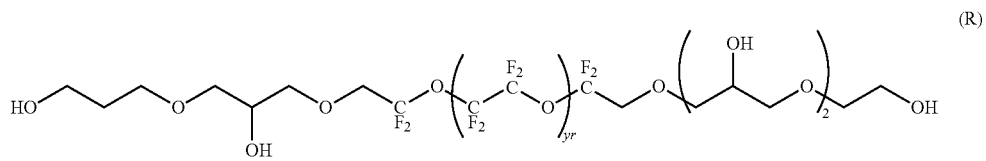
(R)

(In formula (R), yr represents 8.0.)

A $^1$H-NMR measurement of the obtained compound (R) was conducted, and the structure was identified based on the following results.

Compound (R): $^1$H-NMR (CD$_3$COCD$_3$): δ [ppm] 1.6 to 1.8 (2H), 3.4 to 4.2 (32H)

Example 19

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 9 were conducted, yielding 8.24 g of a compound (S) represented by formula (S) shown below.

[Chemical formula 32]

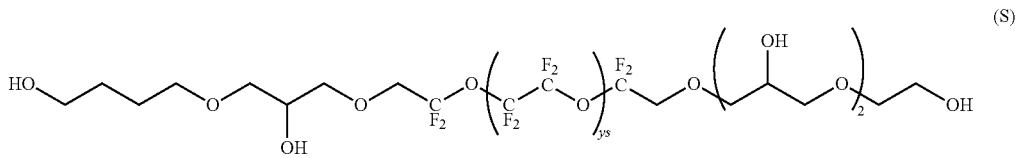

(In formula (S), ys represents 8.0.)

A $^1$H-NMR measurement of the obtained compound (S) was conducted, and the structure was identified based on the following results.

Compound (S): $^1$H-NMR (CD$_3$COCD$_3$): δ [ppm] 1.6 to 1.8 (4H), 3.4 to 4.2 (32H)

Example 20

With the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 10 were conducted, yielding 8.24 g of a compound (T) represented by formula (T) shown below.

[Chemical formula 33]

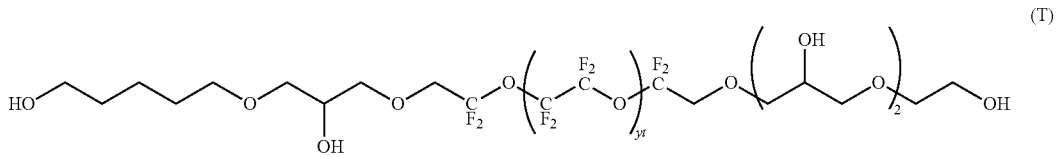

(In formula (T), yt represents 8.0.)

A $^1$H-NMR measurement of the obtained compound (T) was conducted, and the structure was identified based on the following results.

Compound (T): $^1$H-NMR (CD$_3$COCD$_3$): δ [ppm] 1.4 to 1.8 (6H), 3.4 to 4.2 (32H)

Example 21

In the reaction similar to Example 1 described in Example 2, 4.18 g of the compound represented by formula (10) was used instead of the compound represented by formula (7), and by using the same method as Example 2, 11.40 g of a compound represented by formula (16) shown below was obtained as an intermediate instead of the compound represented by formula (21). Subsequently, with the exception of using the compound represented by formula (13) instead of the compound represented by formula (8), the same operations as Example 2 were conducted, yielding 7.59 g of a compound (U) represented by formula (U) shown below.

[Chemical formula 34]

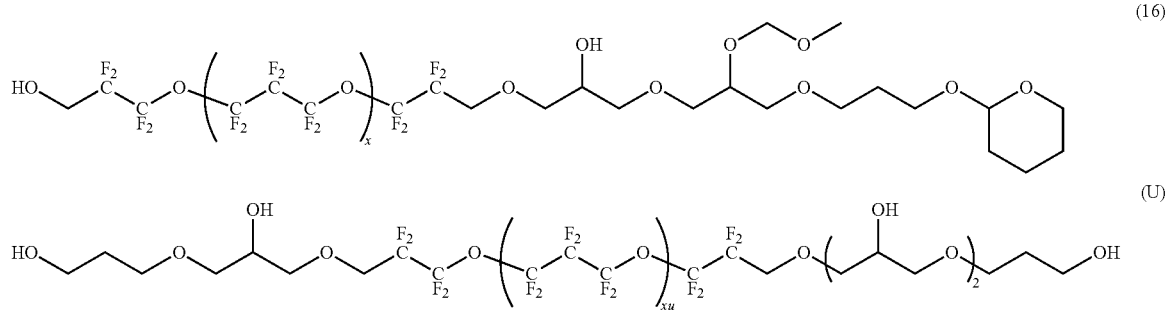

(In formula (16), x represents 5.0.)
(In formula (U), xu represents 5.0.)

A $^1$H-NMR measurement of the obtained compound (U) was conducted, and the structure was identified based on the following results.

Compound (U): $^1$H-NMR (CD$_3$COCD$_3$): δ [ppm] 1.6 to 1.8 (4H), 3.4 to 4.2 (32H)

Example 22

In the reaction similar to Example 1 described in Example 21, with the exception of using 22.12 g of HOCH$_2$CF$_2$O(CF$_2$CF$_2$O)$_y$CF$_2$CH$_2$OH (wherein y in the formula is 8.0) instead of the HOCH$_2$CF$_2$CF$_2$O(CF$_2$CF$_2$CF$_2$O)$_x$CF$_2$CF$_2$CH$_2$OH (wherein x in the formula is 5.0), the same operations as Example 21 were conducted, yielding 10.02 g of a compound (V) represented by formula (V) shown below.

[Chemical formula 35]

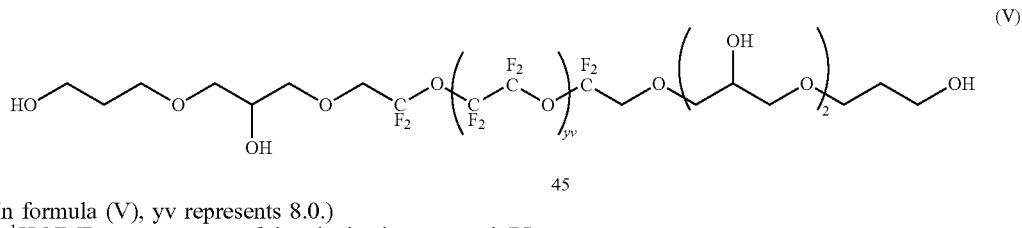

(In formula (V), yv represents 8.0.)

A $^1$H-NMR measurement of the obtained compound (V) was conducted, and the structure was identified based on the following results.

Compound (V): $^1$H-NMR (CD$_3$COCD$_3$): δ [ppm] 1.6 to 1.8 (4H), 3.4 to 4.2 (32H)

Comparative Example 1

A compound (X) represented by formula (X) shown below was synthesized using the method disclosed in Patent Document 1.

[Chemical formula 36]

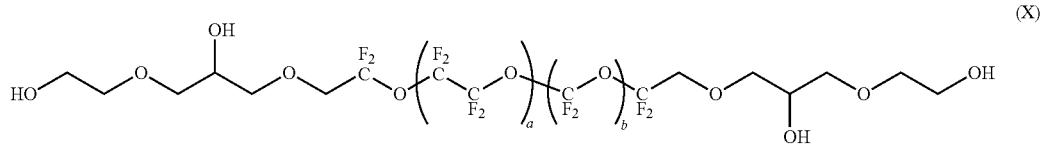

(In formula (X), a represents 5.0 and b represents 5.0.)

A $^1$H-NMR measurement of the obtained compound (X) was conducted, and the structure was identified based on the following results.

Compound (X): $^1$H-NMR (CD$_3$COCD$_3$): δ [ppm]3.4 to 4.2 (26H)

Comparative Example 2

With the exception of using the compound represented by formula (8) instead of the compound represented by formula (7), a compound (Y) represented by formula (Y) shown below was synthesized in the same manner as Example 4.

[Chemical formula 37]

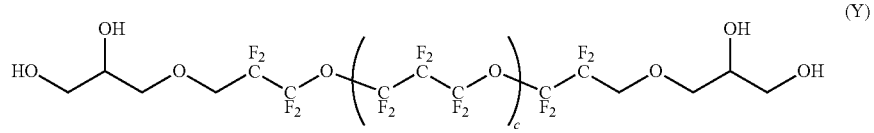

(Y)

(In formula (Y), c represents 5.0.)

A $^1$H-NMR measurement of the obtained compound (Y) was conducted, and the structure was identified based on the following results.

Compound (Y): $^1$H-NMR (CD$_3$COCD$_3$): δ [ppm]3.4 to 4.2 (18H)

Comparative Example 3

A compound (Z) represented by formula (Z) shown below was synthesized using the method disclosed in Patent Document 2.

[Chemical formula 38]

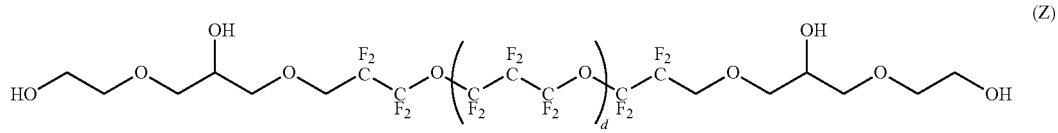

(Z)

(In formula (Z), d represents 5.0.)

A $^1$H-NMR measurement of the obtained compound (Z) was conducted, and the structure was identified based on the following results.

Compound (Z): $^1$H-NMR (CD$_3$COCD$_3$): δ [ppm]3.4 to 4.2 (26H)

The structures of R$^1$ to R$^3$ when the compounds of Examples 1 to 22 and Comparative Examples 1 to 3 obtained in the manner described above are applied to formula (1) are shown in Table 1 and Table 2. Further, the number average molecular weights (Mn) of the compounds of Examples 1 to 22 and Comparative Examples 1 to 3 were determined from the $^1$H-NMR and $^{19}$F-NMR measurements described above. The results are shown in Table 1 and Table 2.

TABLE 1

| Example | Compound | Left terminal (R$^3$) | R$^2$ | Right terminal (R$^1$) | Mn |
|---|---|---|---|---|---|
| 1 | A | HO— | p = 3<br>q = 5.0 | formula (3)<br>n = 1 | 1301 |
| 2 | B | formula (4-1) | p = 3<br>q = 5.0 | formula (3)<br>n = 1 | 1374 |
| 3 | C | formula (4-2)<br>k = 2 | p = 3<br>q = 5.0 | formula (3)<br>n = 1 | 1418 |
| 4 | D | formula (3)<br>n = 1 | p = 3<br>q = 5.0 | formula (3)<br>n = 1 | 1492 |
| 5 | E | formula (3)<br>n = 2 | p = 3<br>q = 5.0 | formula (3)<br>n = 2 | 1520 |
| 6 | F | formula (3)<br>n = 3 | p = 3<br>q = 5.0 | formula (3)<br>n = 3 | 1549 |
| 7 | G | formula (3)<br>n = 4 | p = 3<br>q = 5.0 | formula (3)<br>n = 4 | 1577 |
| 8 | H | formula (4-2)<br>k = 3 | p = 3<br>q = 5.0 | formula (3)<br>n = 1 | 1432 |
| 9 | I | formula (4-2)<br>k = 4 | p = 3<br>q = 5.0 | formula (3)<br>n = 1 | 1446 |
| 10 | J | formula (4-2)<br>k = 5 | p = 3<br>q = 5.0 | formula (3)<br>n = 1 | 1460 |
| 11 | K | HO— | p = 2<br>q = 8.0 | formula (3)<br>n = 1 | 1299 |
| 12 | L | formula (4-1) | p = 2<br>q = 8.0 | formula (3)<br>n = 1 | 1372 |
| 13 | M | formula (4-2)<br>k = 2 | p = 2<br>q = 8.0 | formula (3)<br>n = 1 | 1416 |
| 14 | N | formula (3)<br>n = 1 | p = 2<br>q = 8.0 | formula (3)<br>n = 1 | 1490 |
| 15 | O | formula (3)<br>n = 2 | p = 2<br>q = 8.0 | formula (3)<br>n = 2 | 1518 |
| 16 | P | formula (3)<br>d = 3 | p = 2<br>q = 8.0 | formula (3)<br>n = 3 | 1547 |

TABLE 1-continued

| Example | Compound | Left terminal (R³) | R² | Right terminal (R¹) | Mn |
|---|---|---|---|---|---|
| 17 | Q | formula (3) n = 4 | p = 2 q = 8.0 | formula (3) n = 4 | 1574 |
| 18 | R | formula (4-2) k = 3 | p = 2 q = 8.0 | formula (3) n = 1 | 1430 |
| 19 | S | formula (4-2) k = 4 | p = 2 q = 8.0 | formula (3) n = 1 | 1444 |
| 20 | T | formula (4-2) k = 5 | p = 2 q = 8.0 | formula (3) n = 1 | 1458 |
| 21 | U | formula (4-2) k = 3 | p = 3 q = 5.0 | formula (3) n = 2 | 1446 |
| 22 | V | formula (4-2) k = 3 | p = 2 q = 8.0 | formula (3) n = 2 | 1444 |

TABLE 2

| Comparative Example | Compound | Left terminal | PFPE chain | Right terminal | Mn |
|---|---|---|---|---|---|
| 1 | X | formula (4-2) k = 2 | Fomblin a = b = 5.0 | formula (4-2) k = 2 | 1324 |
| 2 | Y | formula (4-1) | p = 3 q = 5.0 | formula (4-1) | 1256 |
| 3 | Z | formula (4-2) k = 2 | p = 3 q = 5.0 | formula (4-2) k = 2 | 1344 |

Next, using the method described below, the compounds obtained in Examples 1 to 22 and Comparative Examples 1 to 3 were each used to prepare a solution for forming a lubricant layer. Each of the obtained solutions for forming a lubricant layer was then used to form the lubricant layer of a magnetic recording medium in accordance with the method described below, thus obtaining magnetic recording media of Examples 1 to 22 and Comparative Examples 1 to 3.

[Solution for Forming Lubricant Layer]

Each of the compounds obtained in Examples 1 to 22 and Comparative Examples 1 to 3 was dissolved in the fluorine-based solvent Vertrel (a registered trademark) XF (a product name, manufactured by Mitsui DuPont Fluorochemicals Co., Ltd.), and the solution was then diluted with Vertrel XF so that application to a protective layer yielded a film thickness of 9 Å to 10 Å, thus completing preparation of solutions for forming a lubricant layer of Examples 1 to 22 and Comparative Examples 1 to 3.

[Magnetic Recording Medium]

A magnetic recording medium was prepared having an adhesive layer, a soft magnetic layer, a first base layer, a second base layer, a magnetic layer and a protective layer provided sequentially on a substrate having a diameter of 65 mm. The protective layer was formed from carbon.

The solutions for forming a lubricant layer of Examples 1 to 22 and Comparative Examples 1 to 3 were each applied by a dipping method to the protective layer of a magnetic recording medium having each of the above layers up to and including the protective layer already formed. The dipping was performed under conditions of an immersion speed of 10 mm/sec, an immersion time of 30 sec, and a withdrawal speed of 1.2 mm/sec.

Subsequently, the magnetic recording medium with the solution for forming a lubricant layer applied was placed in a 120° C. thermostatic oven and heated for 10 minutes, thereby removing the solvent from the solution for forming a lubricant layer and forming a lubricant layer on the protective layer, thus obtaining magnetic recording media of Examples 1 to 22 and Comparative Examples 1 to 3.

The film thickness of the lubricant layer on each of the magnetic recording media of Examples 1 to 22 and Comparative Examples 1 to 3 obtained in the manner described above was measured using an FT-IR (product name: Nicolet iS50, manufactured by Thermo Fisher Scientific Inc.). The results are shown in Table 4.

Next, for each of the magnetic recording media of Examples 1 to 22 and Comparative Examples 1 to 3, an adhesion (bond ratio) measurement, a pickup suppression test and a chemical substance resistance test were conducted using the methods described below.

(Measurement of Adhesion (Bond Ratio) Between Lubricant Layer and Protective Layer)

The magnetic recording medium having the lubricant layer formed thereon was cleaned by immersion for 10 minutes in the solvent Vertrel XF and subsequent removal from the solvent. The speed with which the magnetic recording medium was immersed in the solvent was 10 mm/sec, and the withdrawal speed was 1.2 mm/sec. Subsequently, the thickness of the lubricant layer was remeasured using the same method as that used for the lubricant layer thickness measurement conducted prior to the cleaning process.

The lubricant layer thickness prior to cleaning was deemed A, the lubricant layer thickness following cleaning (following solvent immersion) was deemed B, and the bond ratio of the lubricant was calculated as the ratio between A and B ((B/A)×100(%)). Using the calculated bond ratio, the adhesion between the lubricant layer and the protective layer was evaluated against the following criteria. The results are shown in Table 4.

[Evaluation of Adhesion (Bond Ratio)]

a: bond ratio of 80% or higher b: bond ratio of at least 70% but less than 80% c: bond ratio of at least 50% but less than 70% d: bond ratio of less than 50%

(Pickup Suppression Test)

The magnetic recording medium and a magnetic head were mounted on a spin stand, and the magnetic head was floated at a fixed point for 10 minutes under normal temperature but reduced pressure conditions (about 250 Torr). Subsequently, the surface of the magnetic head opposing the magnetic recording medium (namely, the surface of the lubricant layer) was analyzed using an ESCA (Electron Spectroscopy for Chemical Analysis) device. Based on the intensity (signal intensity (a.u.)) of the peak derived from fluorine in the ESCA measurement, the amount of lubricant adhered to the magnetic head was evaluated against the criteria shown below in Table 3. The results are shown in Table 4.

TABLE 3

| Evaluation | ESCA signal intensity (a.u.) | Evaluation criteria |
|---|---|---|
| a | 500 or less | No adhesion of lubricant to head. No change in signal intensity |
| b | greater than 500 but no more than 1,000 | Slight adhesion of lubricant to head. Small signal intensity |
| d | greater than 1,000 | Plentiful adhesion of lubricant to head. Large signal intensity |

(Chemical Substance Resistance Test)

This evaluation method was used for investigating the level of contamination of the magnetic recording medium by environmental substances that generate contaminants in high-temperature environments. In the evaluation method described below, Si ions were used as the environmental substance, and the amount of Si adsorption was measured as the amount of contaminants generated from the environmental substance and contaminating the magnetic recording medium.

Specifically, the magnetic recording medium used as the evaluation target was held for 240 hours in a high-temperature environment at a temperature of 85° C. and a humidity of 0% in the presence of a siloxane-based Si rubber. Subsequently, the amount of Si adsorption that existed at the surface of the magnetic recording medium was analyzed and measured by secondary ion mass spectrometry (SIMS), and the level of Si ion contamination was evaluated as the amount of Si adsorption.

Evaluation of the amount of Si adsorption was conducted by deeming the result for the amount of Si adsorption on the magnetic recording medium obtained using the compound Z of Comparative Example 3 as 1.00, and then determining the amount of Si adsorption in each of the examples and comparative examples as a numerical value relative to the level in Comparative Example 3. The results are shown in Table 4.

[Evaluation of Chemical Substance Resistance]
 a: less than 0.85
 b: at least 0.85 but less than 1.0
 c: at least 1.0, but less than 1.2
 d: 1.2 or greater

TABLE 4

| | Compound | Film thickness (Å) | Bond ratio (%) | Pickup resistance | Chemical substance resistance |
|---|---|---|---|---|---|
| Example 1 | A | 9.4 | b | a | b |
| Example 2 | B | 9.5 | b | a | b |
| Example 3 | C | 9.4 | a | a | a |
| Example 4 | D | 9.6 | a | a | a |
| Example 5 | E | 9.5 | a | a | a |
| Example 6 | F | 9.5 | a | a | a |
| Example 7 | G | 9.5 | a | a | a |
| Example 8 | H | 9.3 | a | a | a |
| Example 9 | I | 9.5 | a | a | b |
| Example 10 | J | 9.6 | a | a | b |
| Example 11 | K | 9.5 | b | a | b |
| Example 12 | L | 9.6 | b | a | b |
| Example 13 | M | 9.4 | a | a | a |
| Example 14 | N | 9.5 | a | a | a |
| Example 15 | O | 9.4 | a | a | a |
| Example 16 | P | 9.7 | a | a | a |
| Example 17 | Q | 9.4 | a | a | a |
| Example 18 | R | 9.5 | a | a | a |
| Example 19 | S | 9.6 | a | a | a |
| Example 20 | T | 9.5 | a | a | b |
| Example 21 | U | 9.5 | a | a | a |
| Example 22 | V | 9.6 | a | a | a |
| Comparative Example 1 | X | 9.5 | c | d | c |
| Comparative Example 2 | Y | 9.4 | c | d | c |
| Comparative Example 3 | Z | 9.4 | b | a | c |

As illustrated in Table 4, the magnetic recording media of Examples 1 to 22 exhibited results of b or a for all the evaluations of adhesion (bond ratio), pickup suppression and chemical substance resistance.

It is surmised that these results were able to be achieved because in the magnetic recording media of Examples 1 to 22, the hydroxyl groups of $R^1$ located at one terminal of $R^2$ and $R^3$ located at the other terminal of $R^2$ in the compound represented by formula (1) that forms the lubricant layer adsorb strongly to the protective layer.

In contrast, for the fluorine-containing ether compounds of Comparative Example 1 and Comparative Example 2, the pickup suppression evaluation was d, and the adhesion (bond ratio) and chemical substance resistance evaluations were c.

It is surmised that this is because, in Comparative Example 1, the number of hydroxyl groups bonded at the two terminals of the perfluoropolyether chain was small, meaning the adhesion to the protective layer was unsatisfactory, and moreover, the repeating unit of the perfluoropolyether chain included (—$CF_2$—O—), meaning the rigidity of the perfluoropolyether chain was unsatisfactory, making the compound more likely to aggregate on top of the protective layer. Further, in Comparative Example 2, it is thought that the number of hydroxyl groups bonded at the two terminals of the perfluoropolyether chain was small, meaning the adhesion to the protective layer was unsatisfactory, and moreover, the carbon atoms to which the hydroxyl groups were bonded were bonded to each other, causing the coating properties to be unsatisfactory.

Furthermore, although the fluorine-containing ether compound of Comparative Example 3 had a pickup suppression evaluation of a and an adhesion (bond ratio) evaluation of b, the chemical substance resistance evaluation was c.

It is thought that this is because, in Comparative Example 3, the number of hydroxyl groups bonded at the two terminals of the perfluoropolyether chain was small, meaning the wet spreadability on the protective layer was unsatisfactory.

INDUSTRIAL APPLICABILITY

By using a lubricant for a magnetic recording medium that contains a fluorine-containing ether compound of the present invention, a lubricant layer can be formed that has good adhesion to the protective layer, can suppress pickup, and exhibits excellent chemical substance resistance.

DESCRIPTION OF THE REFERENCE SIGNS

10: Magnetic recording medium
11: Substrate
12: Adhesive layer
13: Soft magnetic layer
14: First base layer
15: Second base layer
16: Magnetic layer
17: Protective layer
18: Lubricant layer

The invention claimed is:
1. A fluorine-containing ether compound represented by formula (Q) shown below:

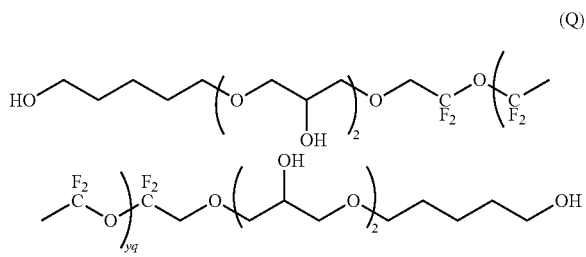

wherein in formula (Q), yq indicates an average polymerization degree, and represents a number from 1 to 20.

2. A lubricant for a magnetic recording medium, the lubricant containing the fluorine-containing ether compound according to claim 1.

3. A magnetic recording medium comprising at least a magnetic layer, a protective layer and a lubricant layer provided sequentially on a substrate, wherein the lubricant layer contains the fluorine-containing ether compound according to claim 1.

4. A fluorine-containing ether compound represented by formula (T) shown below:

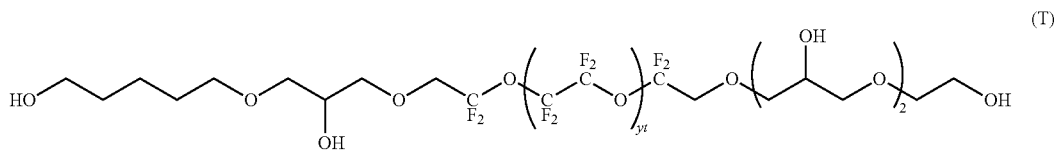

wherein
in formula (T), yt indicates the average polymerization degree, and represents a number from 1 to 20.

5. A lubricant for a magnetic recording medium, the lubricant containing the fluorine-containing ether compound according to claim 4.

6. A magnetic recording medium comprising at least a magnetic layer, a protective layer and a lubricant layer provided sequentially on a substrate, wherein the lubricant layer contains the fluorine-containing ether compound according to claim 4.

7. A fluorine-containing ether compound represented by formula (A) shown below:

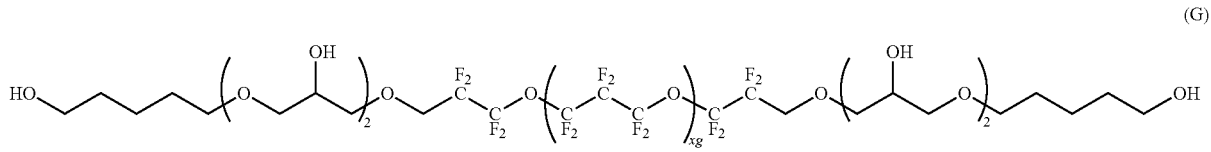

wherein
in formula (G), xg indicates the average polymerization degree, and represents a number from 1 to 14,

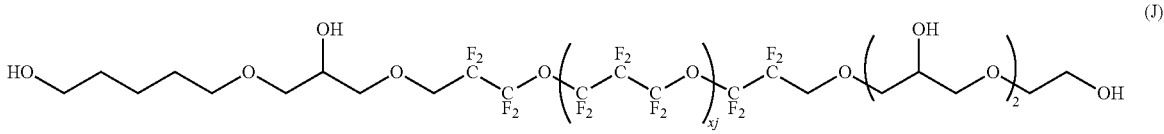

wherein
in formula (J), xj indicates the average polymerization degree, and represents a number from 1 to 14.

8. A lubricant for a magnetic recording medium, the lubricant containing the fluorine-containing ether compound according to claim 7.

9. A lubricant for a magnetic recording medium according to claim 8, wherein the amount of the fluorine-containing ether compound within the lubricant is 70% by mass or greater.

10. A magnetic recording medium comprising at least a magnetic layer, a protective layer and a lubricant layer the lubricant containing the fluorine-containing ether compound according to claim 7. provided sequentially on a substrate, wherein the lubricant layer contains the fluorine-containing ether compound according to claim 7.

* * * * *